(12) United States Patent
Martin et al.

(10) Patent No.: US 11,788,051 B2
(45) Date of Patent: Oct. 17, 2023

(54) CELL SEPARATION DEVICE AND METHOD FOR USING SAME

(71) Applicant: Corning Incorporated, Corning, NY (US)

(72) Inventors: Gregory Roger Martin, Acton, ME (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 1292 days.

(21) Appl. No.: 16/061,964

(22) PCT Filed: Dec. 13, 2016

(86) PCT No.: PCT/US2016/066327
§ 371 (c)(1),
(2) Date: Jun. 13, 2018

(87) PCT Pub. No.: WO2017/112455
PCT Pub. Date: Jun. 29, 2017

(65) Prior Publication Data
US 2020/0270565 A1 Aug. 27, 2020

Related U.S. Application Data

(60) Provisional application No. 62/270,950, filed on Dec. 22, 2015.

(51) Int. Cl.
| | | |
|---|---|---|
| C12M 1/00 | (2006.01) | |
| C12M 1/26 | (2006.01) | |
| C12N 5/00 | (2006.01) | |

(52) U.S. Cl.
CPC ............ C12M 47/02 (2013.01); C12M 33/14 (2013.01); C12N 5/0075 (2013.01)

(58) Field of Classification Search
None
See application file for complete search history.

(56) References Cited

U.S. PATENT DOCUMENTS

| | | | |
|---|---|---|---|
| 4,191,182 A | 3/1980 | Popovich et al. | |
| 4,194,976 A | 3/1980 | Robinsky | |
| 5,820,767 A | 10/1998 | Kane et al. | |
| 6,461,513 B1 | 10/2002 | Jen | |
| 9,296,984 B2 | 3/2016 | Cimino et al. | |
| 9,376,655 B2* | 6/2016 | Larsen ................... | C12M 33/14 |
| 2008/0105605 A1 | 5/2008 | Kobayashi | |
| 2008/0302712 A1 | 12/2008 | Laverdiere et al. | |
| 2010/0078395 A1 | 4/2010 | Shevitz | |
| 2011/0070648 A1* | 3/2011 | Anneren ................ | C12M 25/16 |
| | | | 435/380 |
| 2013/0071304 A1 | 3/2013 | Jeon | |
| 2013/0081995 A1* | 4/2013 | Larsen ................... | B01D 29/13 |
| | | | 210/443 |
| 2013/0157353 A1* | 6/2013 | Dijkhuizen Borgart et al. ........... | |
| | | | C12M 23/14 |
| | | | 435/297.2 |
| 2013/0164731 A1 | 6/2013 | Cimino et al. | |
| 2014/0287512 A1 | 9/2014 | Kaisermayer et al. | |
| 2015/0060360 A1 | 3/2015 | Motherway et al. | |
| 2018/0169547 A1 | 6/2018 | Lacey | |

FOREIGN PATENT DOCUMENTS

| | | |
|---|---|---|
| DE | 3406928 A1 | 9/1984 |
| EP | 2590695 A2 | 5/2013 |
| EP | 2848293 A1 | 3/2015 |
| JP | 62-110713 A | 5/1987 |
| JP | 2000-517171 A | 12/2000 |
| JP | 2012065590 A | 4/2012 |
| WO | 2011025890 A1 | 3/2011 |
| WO | 2012/006587 A2 | 1/2012 |
| WO | 2012158108 A1 | 11/2012 |
| WO | 2013055517 A1 | 4/2013 |
| WO | 2014/093439 A1 | 6/2014 |
| WO | 2015/145793 A1 | 10/2015 |
| WO | 2016/200850 A1 | 12/2016 |

OTHER PUBLICATIONS

Japanese Patent Application No. 2018-532641 Office Action dated Sep. 2, 2020, 9 pages (4 pages of English Translation and 5 pages of Original Document); Japanese Patent Office.
"Microcarrier Bead Separation and Cell Harvest Using Thermo Scientific HYQ Harvestainer." Thermo Scientific Inc., Application Notes AN012, pp. 1-3, 2012.
"IPS: Inclined Plate Settlers." Metso Corporation, Brochure No. 1223-06-11-ESBL/SALA—English, 8 Pages, 2014.
Dvorak, B., et la., "Drinking Water Treatment: Sediment Filtration." Nebguide, Nebraska Extension, http://extensionpublications.unl.edu/assets/html/g1492/build/g1492.htm, 4 Pages, Revised Dec. 2013, Retrieved Aug. 14, 2017.
International Search Report and Written Opinion of the International Searching Authority; PCT/US2016/066327; dated Aug. 24, 2017; 14 Pages; European Patent Office.

(Continued)

*Primary Examiner* — Vera Afremova
(74) *Attorney, Agent, or Firm* — Chandra J. Duncan

(57) ABSTRACT

A cell separation device configured for separating cells from microcarriers or spheroids in a liquid is provided. The cell separation device includes a vessel comprising a first port, a second port, and a cavity; and a porous mesh disposed within the cavity to divide the cavity into a first compartment and a second compartment, wherein the first port is in communication with the first compartment of the cavity, the first port located to a first side of the porous mesh, wherein the second port is in communication with the second compartment of the cavity, the second port located to a second side of the porous mesh, and wherein the porous mesh is positioned within the cavity to have a substantially vertical orientation or an inclined orientation with respect to a flow of liquid through the porous mesh.

9 Claims, 14 Drawing Sheets

(56) References Cited

OTHER PUBLICATIONS

Spaltro, G., et al., "Characterization of the Pall Celeris System as a Point-Of-Care Device for Therapeutic Angiogenesis." Cytotherapy, vol. 17, Issue 9, pp. 1302-1313, Sep. 2015.
"Steriflip® Filter Units." Emd Millipore, http://emdmillipore.com/us/en/product/steriflip-filter-units,mm_nf-c3238, 2 Pages, Retrieved Nov. 6, 2015.
"Thermo Scientific HyQ Harvestainer BPC." Thermo Scientific Inc., www.thermoscientific.com/harvestainer, 6 Pages, 2012.
"Falcon® 70μM Cell Strainer, White, Sterile, Individually Packaged, 50/Case (Product #352350)." Product Data Sheet, Corning Incorporated, 1 Page, Retrieved Feb. 2018.
"Filtertek Pre-Bypass Filters." Product No. 0072780-00-210, Filtertek Flow Control and Filtration Products, 2 Pages, Retrieved Feb. 16, 2018.
European Patent Application No. 16871765.0 Office Action dated Jun. 26, 2020; 4 Pages; European Patent Office.

\* cited by examiner

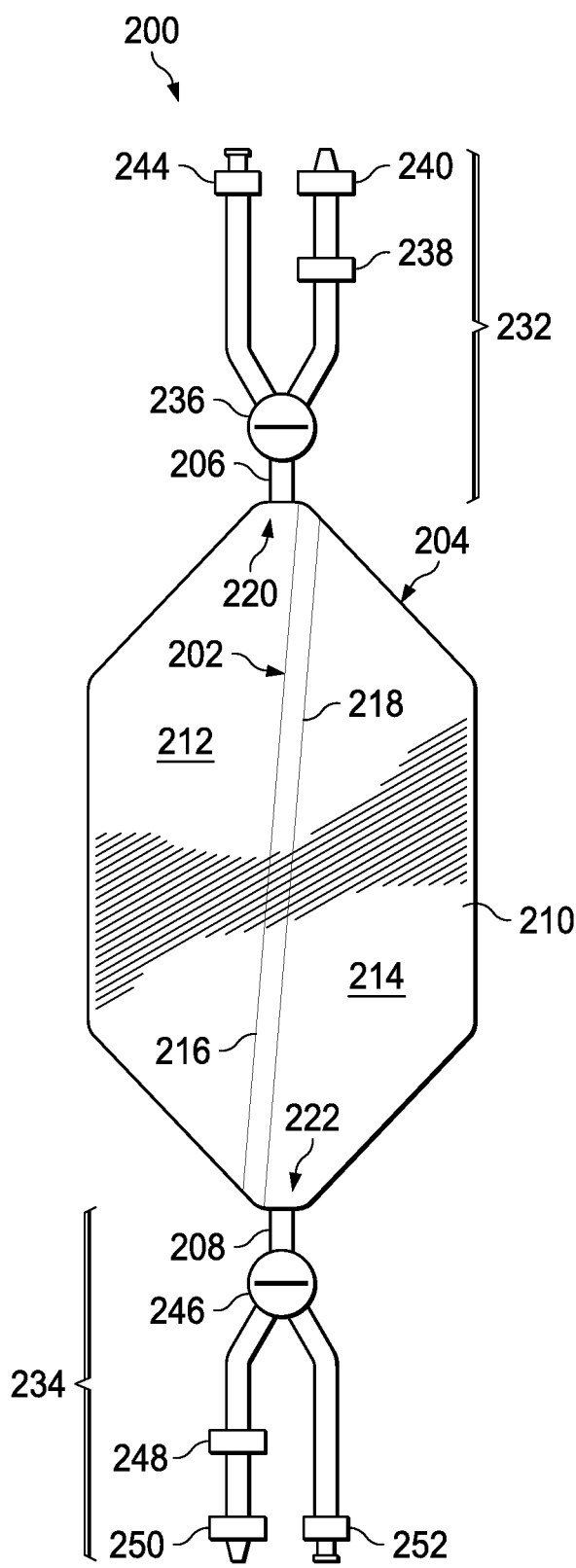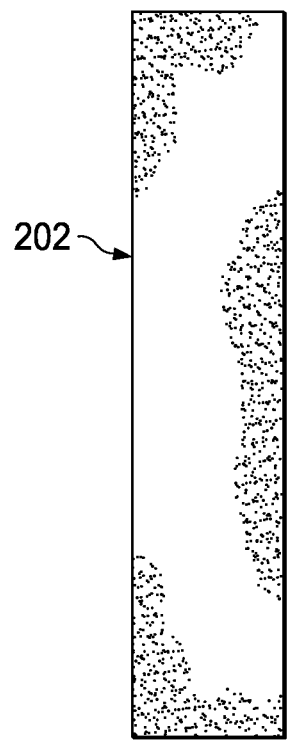
FIG. 2A
FIG. 2B

FIG. 3A                    FIG. 3B

CELL SEPARATION DEVICE AND METHOD FOR USING SAME

CROSS-REFERENCE TO RELATED APPLICATIONS

This is a national stage application under 35 U.S.C. § 371 of International Application No. PCT/US2016/066327, filed on Dec. 13, 2016, which claims the benefit of priority of U.S. Provisional Application Ser. No. 62/270,950 filed Dec. 22, 2015, the content of which is relied upon and incorporated herein by reference in its entirety.

TECHNICAL FIELD

The present disclosure relates to a cell separation device and a method for using the cell separation device to separate cells from microcarriers or spheroids in a liquid (e.g., cell culture medium).

BACKGROUND

There are a several known techniques for separating cells from microcarriers located within a cell culture medium, including for example differential gradient centrifugation, acoustic resonance, tangential flow filtration, spin filters and sedimentation using conical or inclined plates. Most of these known techniques require expensive capital equipment or are complex to operate. Two of the less complex and commercially available devices for separating cells from microcarriers and potentially from spheroids located in a cell culture medium are the Steriflip Filter unit and the HyQ Harvestainer.

The Steriflip Filter unit is designed to work by attaching the unit to a standard 50 milliliter centrifuge tube which contains the cell culture medium (including the microcarriers), flipping the unit over, applying a vacuum such that the filtered cells collect in the attached 50 milliliter centrifuge tube. The Steriflip Filter unit is manufactured by EMDMillipore The HyQ Harvestainer which is manufactured by Thermo Scientific is able to accommodate hundreds of liters of medium and depends upon a pump to perfuse the cells, microcarriers and culture medium through the device. More specifically, the HyQ Harvestainer has a mesh bag inside a larger structured liquid impermeable bag that has an outlet for the perfused media. The microcarriers are repeatedly washed and the cells are enzymatically separated from the microcarriers in an external bioreactor before the solution of cells, microcarriers, and medium are perfused into and through the HyQ Harvestainer. The microcarriers are retained in the inner mesh bag of the HyQ Harvestainer, and the cells and medium pass through the inner mesh bag and then out of the structured outer bag into a cell collection container. As can be appreciated, the steps required make use of the HyQ Harvestainer are cumbersome.

These filtration units and other standard filtration units all position the porous mesh in a horizontal configuration so as to be perpendicular to the flow of the cell culture medium. Thus, when a standard filtration unit is used the flow of the cell culture medium through the horizontally orientated porous mesh is easily blocked because the microcarriers or spheroids land on the horizontal porous mesh and block the pores within the horizontal orientated porous mesh. This problem and other problems are addressed by the present disclosure.

SUMMARY

A cell separation device, and a method for using the cell separation device are described in the independent claims of the present application. Advantageous embodiments of the cell separation device and the method for using the cell separation device are described in the dependent claims.

In one aspect, the present disclosure provides a cell separation device configured for separating cells from microcarriers or spheroids in a liquid. The cell separation device comprises a vessel having a first port, a second port, and a cavity. The cell separation device further comprises a porous mesh disposed within the cavity to divide the cavity into a first compartment and a second compartment. The first port is in communication with the first compartment of the cavity. Further, the first port is located to a first side of the porous mesh. The second port is in communication with the second compartment of the cavity. Further, the second port is located to a second side of the porous mesh. The porous mesh is positioned within the cavity to have a substantially vertical orientation or an inclined orientation with respect to a flow of the liquid through the porous mesh. The cell separation device by having the vertical or inclined porous mesh is a marked-improvement over the traditional cell separation devices in that when the new cell separation device is used the flow of the liquid through the vertical or inclined porous mesh is no longer easily blocked as in the traditional cell separation device because the microcarriers or spheroids will no longer block a majority of the pores within the vertical or inclined porous mesh due to gravity as they would in the horizontal porous mesh of the traditional cell separation devices.

In another aspect, the present disclosure provides a method for using the cell separation device to separate cells from microcarriers or spheroids in a liquid. The method comprises the steps of (a): introducing liquid through a first port of a vessel of a cell separation device, the vessel further comprising a second port, and a cavity, wherein a porous mesh is disposed within the cavity to have a substantially vertical or an inclined orientation with respect to a flow of the liquid through the porous mesh and to divide the cavity into a first compartment and a second compartment, wherein the first port located to a first side of the porous mesh, and wherein the first port is in communication with the first compartment of the cavity and the second port is in communication with the second compartment of the cavity; (b) draining the liquid that passes through the porous mesh out of the second port; (c) processing the microcarriers or spheroids that does not pass through the porous mesh to release the cells from the microcarriers or spheroids; and (d) draining the cells out of the second port. The cell separation device by having the vertical or inclined porous mesh is a marked-improvement over the traditional cell separation devices in that when the new cell separation device is used the flow of the liquid through the vertical or inclined porous mesh is no longer easily blocked as in the traditional cell separation device because the microcarriers or spheroids will no longer block a majority of the pores within the vertical or inclined porous mesh due to gravity as they would in the horizontal porous mesh of the traditional cell separation devices.

Additional aspects of the present disclosure will be set forth, in part, in the detailed description, figures and any claims which follow, and in part will be derived from the detailed description, or can be learned by practice of the disclosure. It is to be understood that both the foregoing general description and the following detailed description are exemplary and explanatory only and are not restrictive of the disclosure as disclosed.

BRIEF DESCRIPTION OF THE DRAWINGS

A more complete understanding of the present disclosure may be had by reference to the following detailed description when taken in conjunction with the accompanying drawings wherein:

FIGS. 2A-2B respectively illustrate a front view of a cell separation device and a side view of a porous mesh that is located within the cell separation device in accordance with an embodiment of the present disclosure;

FIGS. 3A-3C illustrate a cell separation device configured in accordance with an embodiment of the present disclosure;

DETAILED DESCRIPTION

Figure 1A:
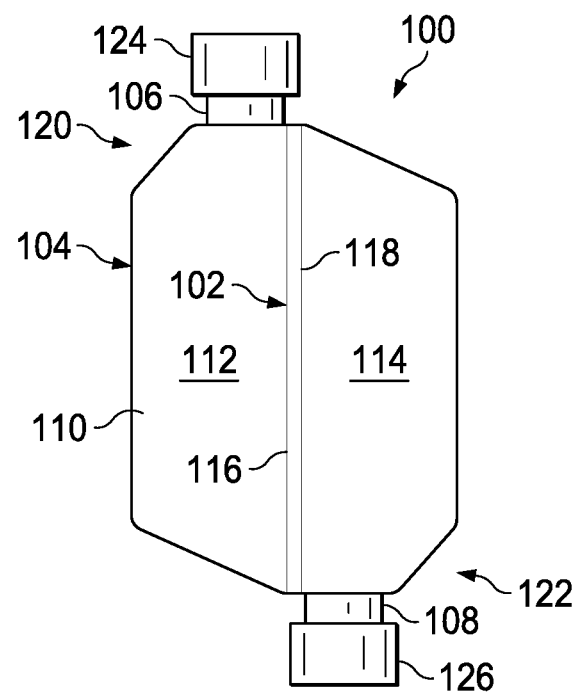
FIGS. 1A-1B respectively illustrate a front view of a cell separation device and a side view of a porous mesh that is located within the cell separation device in accordance with an embodiment of the present disclosure.

Disclosed herein is a cell separation device configured for separating cells from microcarriers or spheroids in a liquid (e.g., cell culture media, buffered saline). The cell separation device comprises a vessel having a first port, a second port, and a cavity. The cell separation device further comprises a porous mesh (liquid permeable membrane etc. . . . ) disposed within the cavity to divide the cavity into a first compartment and a second compartment. The first port is in communication with the first compartment of the cavity. Further, the first port is located to a first side of the porous mesh. The second port is in communication with the second compartment of the cavity. Further, the second port is located to a second side of the porous mesh. The porous mesh is positioned within the cavity to have a substantially vertical orientation or an inclined orientation rather than a horizontal orientation with respect to a flow of the liquid through the porous mesh.

Also disclosed herein is a method for using the new cell separation device to separate cells from microcarriers or spheroids in a liquid (e.g., cell culture medium, buffered saline). The method comprises the steps of (a): introducing liquid through a first port of a vessel of a cell separation device, the vessel further comprising a second port, and a cavity, wherein a porous mesh is disposed within the cavity to have a substantially vertical or an inclined orientation with respect to a flow of the liquid through the porous mesh and to divide the cavity into a first compartment and a second compartment, wherein the first port located to a first side of the porous mesh, and wherein the first port is in communication with the first compartment of the cavity and the second port is in communication with the second compartment of the cavity; (b) draining the liquid that passes through the porous mesh out of the second port; (c) processing the microcarriers or spheroids that does not pass through the porous mesh to release the cells from the microcarriers or spheroids; and (d) draining the cells out of the second port. The cell separation device by having the vertical or inclined porous mesh is a marked-improvement over the traditional cell separation devices in that when the new cell separation device is used the flow of the liquid through the vertical or inclined porous mesh is no longer easily blocked as in the traditional cell separation device because the microcarriers or spheroids will no longer block a majority of the pores within the vertical or inclined porous mesh due to gravity as they would in the horizontal porous mesh of the traditional cell separation devices.

Embodiments of the disclosure will be discussed with reference to FIGS. 1-8, which illustrate various cell separation devices and methods for using the various cell separation device according to non-limiting embodiments of the disclosure. The following description is intended to provide an enabling description of the new cell separation device and the various aspects of the new cell separation device will be specifically discussed in detail throughout the disclosure with reference to the non-limiting embodiments, these embodiments being interchangeable with one another within the context of the disclosure. Although the various cell separation devices described herein are done with reference to separating cells from microcarriers or spheroids in a liquid it should be appreciated that the new cell separation device can be used in other applications such as (for example) straining cells that are stuck together.

Figure 1B:
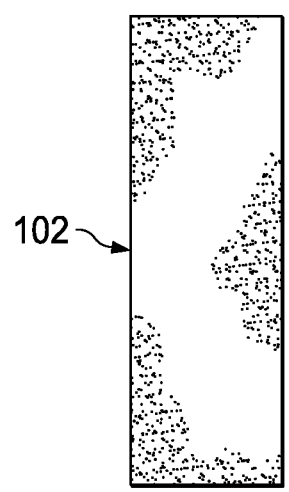

Referring to FIGS. 1A-1B, there are respectively illustrated a front view of a cell separation device 100 and a side view of a porous mesh 102 that is located within the cell separation device 100 in accordance with an embodiment of the present disclosure. As shown, the cell separation device 100 comprises a vessel 104 having a first port 106, a second port 108, and a cavity 110. The cell separation device 100 further comprises the porous mesh 102 disposed within the cavity 110 so as to divide the cavity 110 into a first compartment 112 and a second compartment 114. The first port 106 is in communication with the first compartment 112 of the cavity 110. Further, the first port 106 is located to a first side 116 of the porous mesh 102. The second port 108 is in communication with the second compartment 114 of the cavity 110. Further, the second port 108 is located to a second side 118 of the porous mesh 102. In addition, the first port 106 is located at one end 120 of the vessel 104 and the second port 108 is located at an opposing end 122 of the vessel 104. Also, the first port 106 and the second port 108 are off-set from one another on the vessel 104 such that the porous mesh 102 has the substantially vertical orientation within the cavity 110 when (1) the first port 106 is located in a substantially upward orientation and the second port 108 is located in a substantially downward orientation (as shown in FIG. 1A), or (2) the first port 106 is located in the substantially downward orientation and the second port 108 is located in the substantially upward orientation.

In this example, the cell separation device 100 is configured to be an open-system cell separation device 100 because it is not directly connected to external equipment such as a bioreactor, vacuum pump etc. . . . . In this configuration, the cell separation device 100 has a first cap 124 that is attachable to the first port 106 (i.e., the first cap 124 can be secured to the first port 106 or removed from the first port 106). Further, the cell separation device 100 has a second cap 126 that is attachable to the second port 108 (i.e., the second cap 126 can be secured to the second port 108 or removed from the second port 108).

Figure 1C:
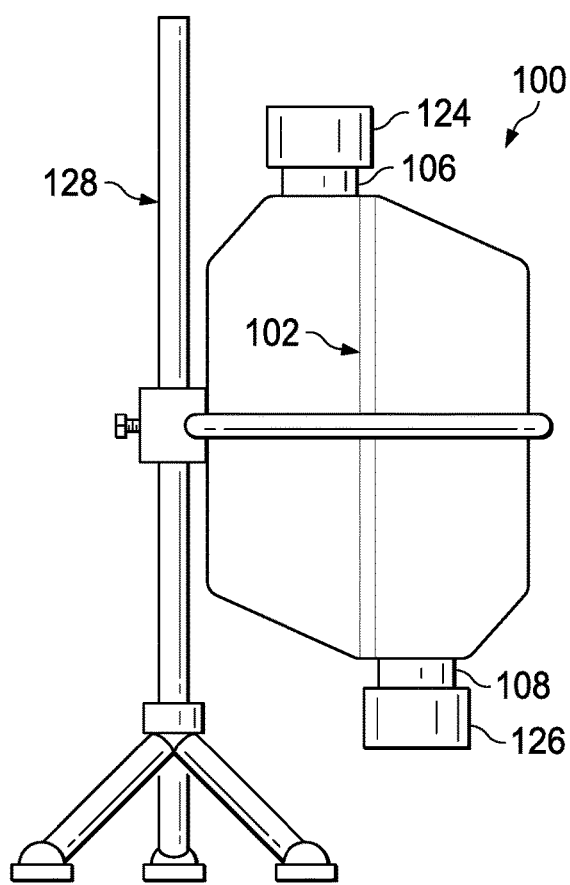
FIG. 1C illustrates a ring stand that can be used to hold and move the cell separation device shown in FIG. 1A in accordance with an embodiment of the present disclosure.
Figure 1D:
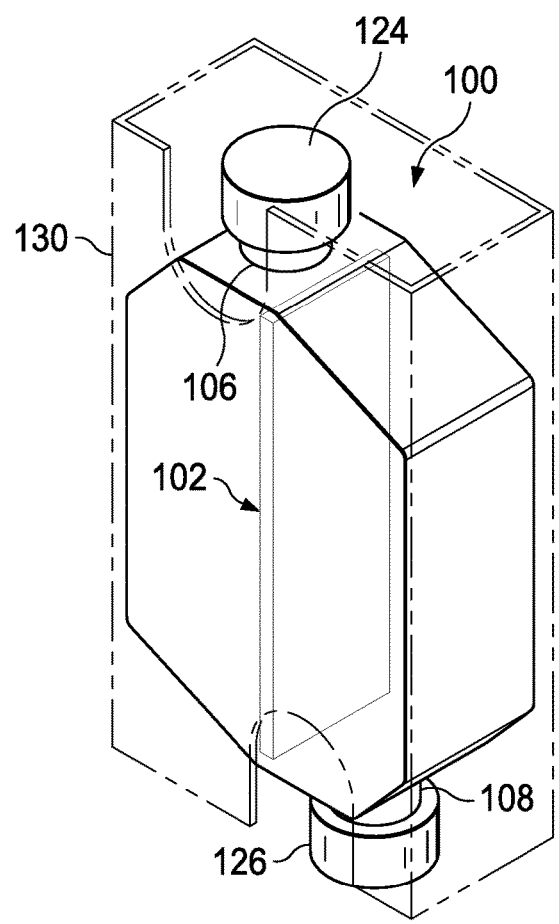
FIG. 1D illustrates an housing that surrounds a large portion of the cell separation device shown in FIG. 1A in accordance with an embodiment of the present disclosure.

As shown in FIG. 1C, a ring stand 128 or similar device can if desired be used to hold and move the cell separation device 100 into anyone of a number of positions when separating cells from microcarriers or spheroids in a liquid (e.g., cell culture medium, buffered saline). Also, FIG. 1D illustrates a housing 130 that can be used if desired that surrounds a large portion of the cell separation device 100 except for the first port 106 and the second port 108. The housing 130 permits the rotation of the cell separation device 100 (which may have a flexible vessel 104) and in general aid in the handling of the cell separation device 100.

In one exemplary application, one can use the cell separation device 100 to obtain the cells from the microcarriers or spheroids within the liquid by performing the following steps:

1) Take off the first cap 124 from the first port 106 on top of the cell separation device 100 which is in an upward orientation.

2) Pour the liquid which includes the microcarriers or spheroids through the first port 106 into the cell separation device 100.

3) Replace the first cap 124 on the first port 106 on top of the cell separation device 100. Then, invert the cell separation device 100 by using for example the aforementioned ring stand 128 such that the first cap 124 is now in a downward orientation and the second cap 126 is now in an upward orientation.

4) Remove the second cap 126 from second port 108 of the cell separation device 100. Then, pour the liquid that passed through the porous mesh 102 out of the second port 108 of the cell separation device 100. Note: that during this pour step the porous mesh 102 retains the microcarriers or spheroids inside the cell separation device 100.

5) Place the second cap 126 on the second port 108 of the cell separation device 100. Then, invert the cell separation device 100 by using for example the aforementioned ring stand 128 such that the first cap 124 is now in an upward orientation and the second cap 126 is now in a downward orientation.

6) Take off the first cap 124 from the first port 106 of the cell separation device 100. Then, pour a washing solution (e.g., phosphate buffered saline (PBS)) through the first port 106 into the cell separation device 100.

7) Replace the first cap 124 on the first port 106 of the cell separation device 100. Move the cell separation device 100. Then, invert the cell separation device 100 by using for example the aforementioned ring stand 128 such that the first cap 124 is now in a downward orientation and the second cap 126 is now in an upward orientation.

8) Remove the second cap 126 from second port 108 of the cell separation device 100. Then, pour the washing solution that passed through the porous mesh 102 out of the second port 108 of the cell separation device 100. Note: steps 6, 7 and 8 can be repeated multiple times. Alternatively, steps 6, 7, and 8 can be omitted.

9) Place the second cap 126 on the second port 108 of the cell separation device 100. Then, invert the cell separation device 100 by using for example the aforementioned ring stand 128 such that the first cap 124 is now in an upward orientation and the second cap 126 is now in a downward orientation.

10) Take off the first cap 124 from the first port 106 of the cell separation device 100. Then, pour a cell dissociation reagent (e.g., trypsin) through the first port 106 into the cell separation device 100.

11) Place the first cap 124 onto the first port 106 of the cell separation device 100. Move the cell separation device 100 into a horizontal position to allow the microcarriers or spheroids to incubate in the cell dissociation reagent. After the cells dissociate, invert the cell separation device 100 by using for example the aforementioned ring stand 128 such that the first cap 124 is now in a downward orientation and the second cap 126 is now in an upward orientation.

12) Remove the second cap 126 from second port 108 of the cell separation device 100. Then, pour the cell dissociation reagent and cells (released from the microcarriers or dissolved from the spheroids) that passed through the porous mesh 102 out of the second port 108 in the cell separation device 100.

Referring to FIGS. 2A-2B, there are respectively illustrated a front view of a cell separation device 200 and a side view of a porous mesh 202 that is located within the cell separation device 200 in accordance with an embodiment of the present disclosure. In this embodiment, the cell separation device 200 comprises a vessel 204 having a first port 206, a second port 208, and a cavity 210. The cell separation device 200 further comprises the porous mesh 202 disposed within the cavity 210 to divide the cavity 210 into a first compartment 212 and a second compartment 214. The first port 206 is in communication with the first compartment 212 of the cavity 210. Further, the first port 206 is located to a first side 216 of the porous mesh 202. The second port 208 is in communication with the second compartment 214 of the cavity 210. Further, the second port 208 is located to a second side 218 of the porous mesh 202. In addition, the first port 206 is located at one end 220 of the vessel 204 and the second port 208 is located at an opposing end 222 of the vessel 204. Also, the first port 206 and the second port 208 are in-line with one another on the vessel 204 such that the porous mesh 202 has the inclined orientation within the cavity 210 when (1) the first port 206 is located in a substantially upward orientation and the second port 208 is located in a substantially downward orientation (as shown in FIG. 2A), or (2) the first port 206 is located in the substantially downward orientation and the second port 208 is located in the substantially upward orientation. In this exemplary embodiment, the cell separation device 200 can also have a housing (not shown) that surrounds a large portion of the cell separation device 200 except for the first port 206 and the second port 208 (see FIG. 1A for an exemplary housing 130 that could be used with the cell separation device 200). If used, the housing would permit the rotation of the cell separation device 200 (which may have a flexible vessel 104) and in general aid in the handling of the cell separation device 200.

In this example, the cell separation device 200 is configured to be a closed-system cell separation device 200 because it can be directly connected to external equipment such as a bioreactor, vacuum pump etc. . . . as discussed in more detail next with respect to FIGS. 2C-2D. In this configuration, the cell separation device 200 has a first flow control system 232 attached to the first port 206, and a second flow control system 234 attached to the second port 208. In this example, the first flow control system 232 has a valve 236 having one end connected via tubing to the first port 206 and another end connected via Y-shaped tubing to (1) a first clamp 238 (or valve) and a vent filter 240, and (2) a multipurpose connector 244 (or aseptic connector 244). The second flow control system 234 has a valve 246 having one end connected via tubing to the second port 208 and another end connected via Y-shaped tubing to (1) a first clamp 248 (or valve) and a vent filter 250, and (2) a multipurpose connector 252 (or aseptic connector 252). The vent filters 240 and 250 can be opened to permit air to escape from the cell separation device 200.

Figure 2C:
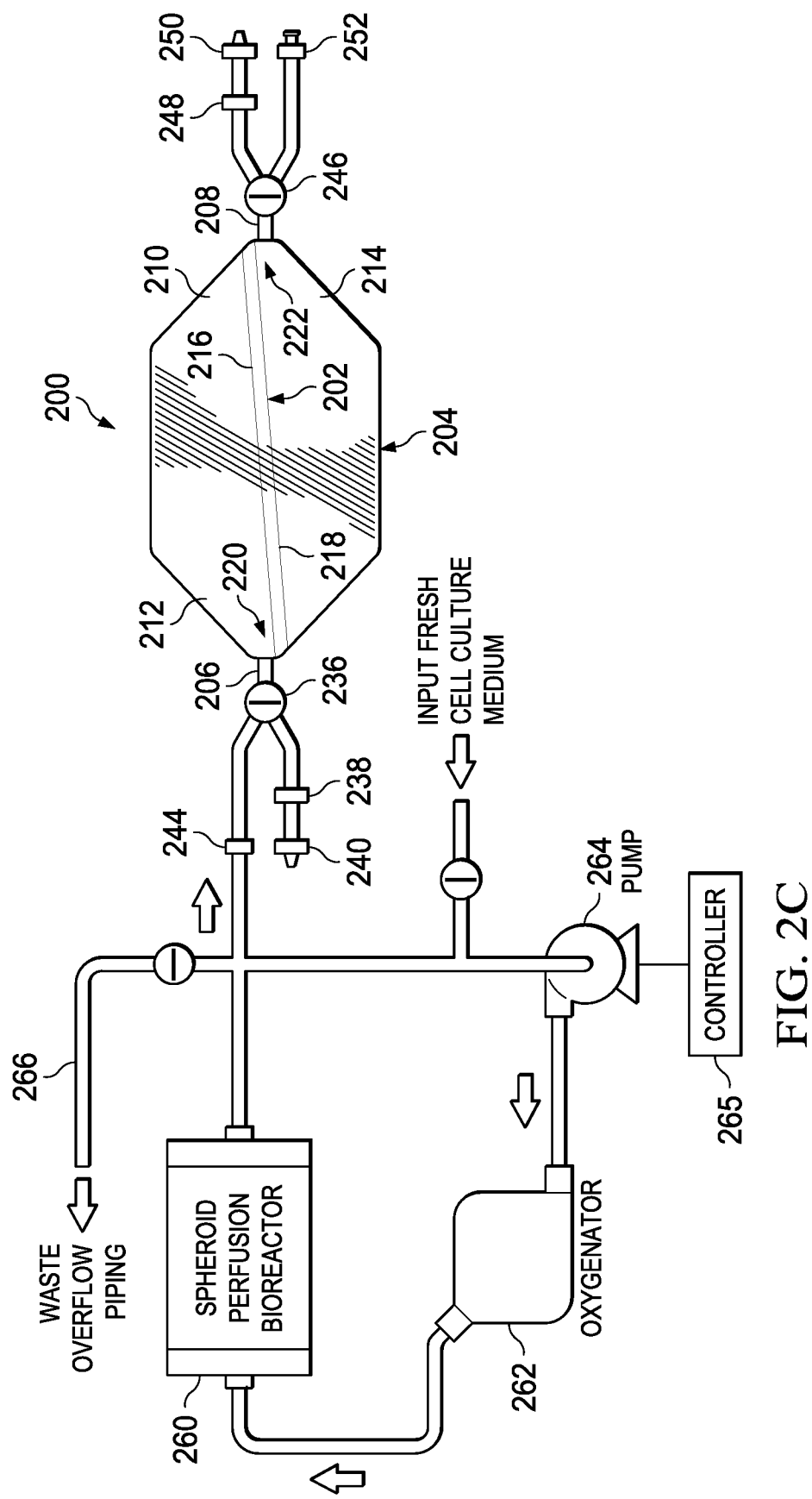
FIGS. 2C-2D illustrate two different external systems coupled to the cell separation device shown in FIG. 2A in accordance with an embodiment of the present disclosure.
Figure 2D:
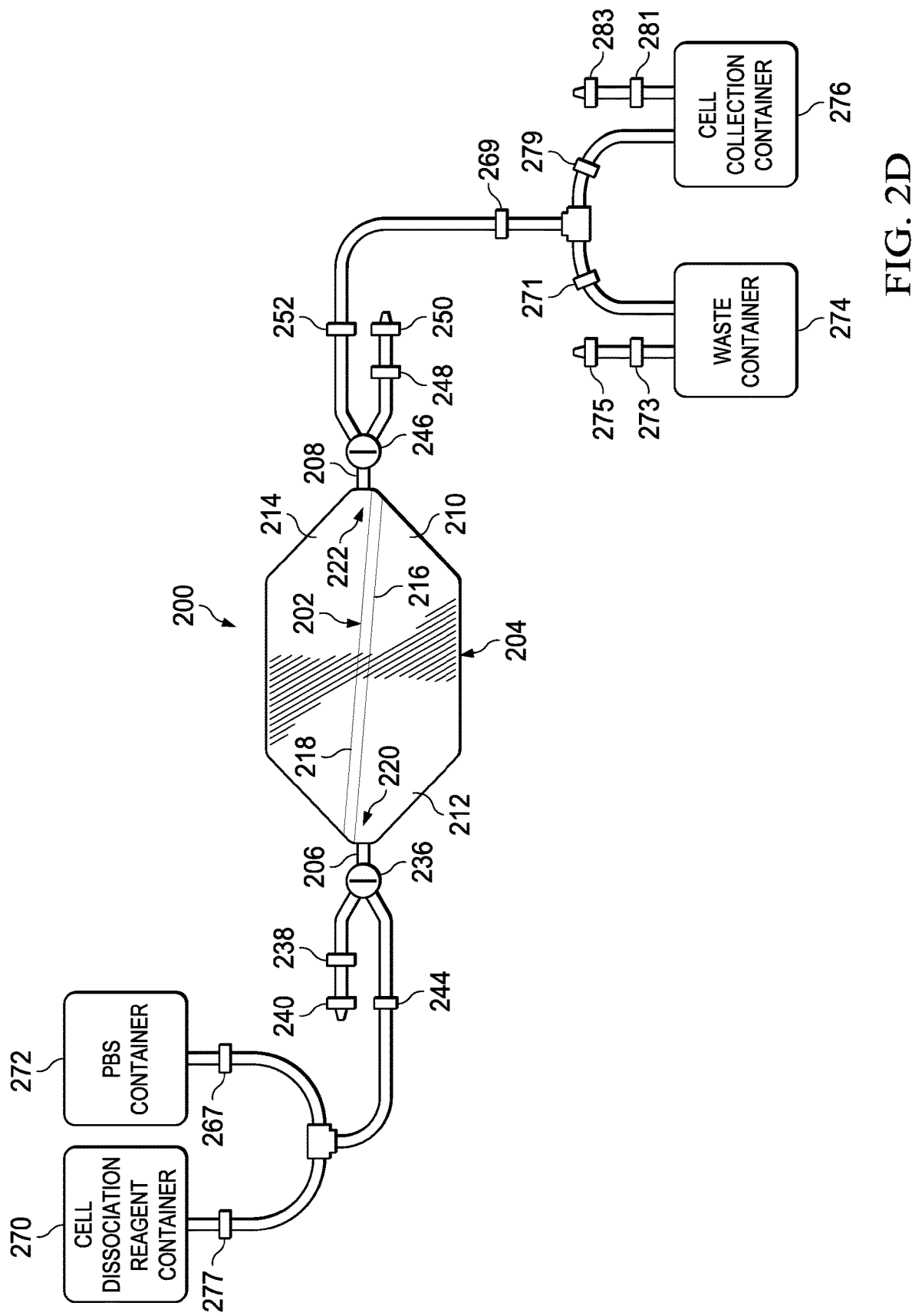
Figure 3C:
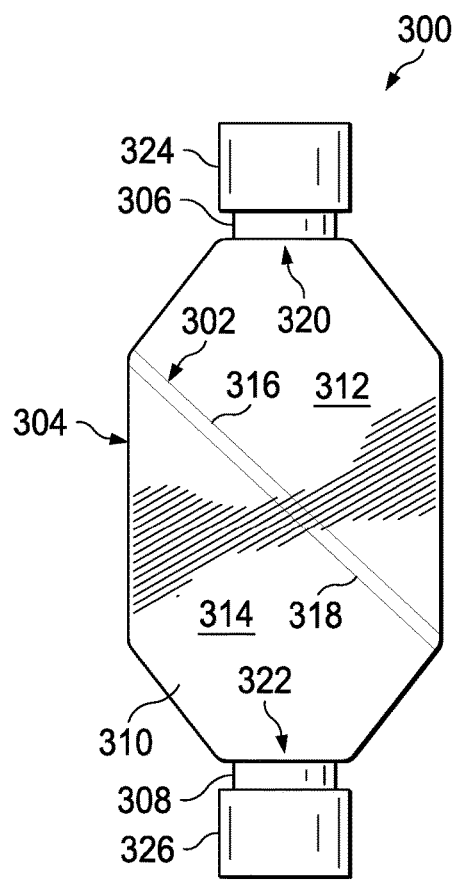
Figure 3C:
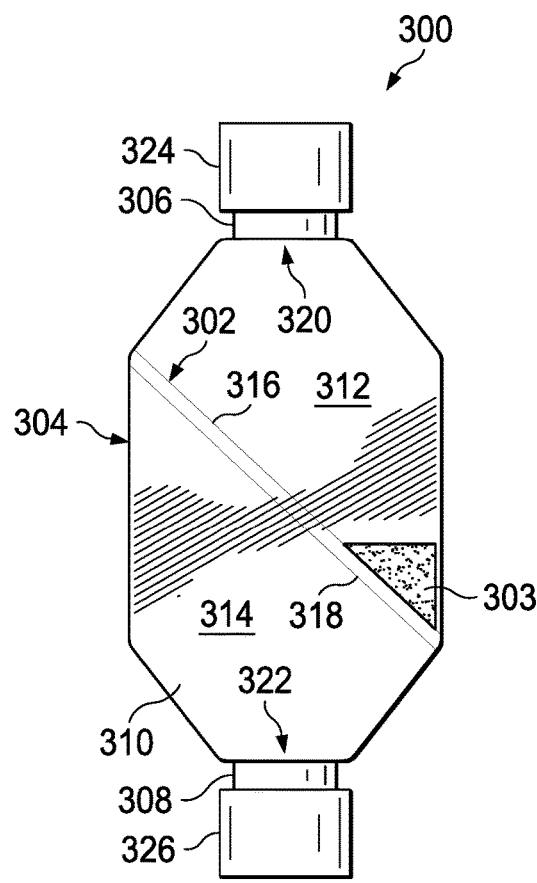
Figure 3C:
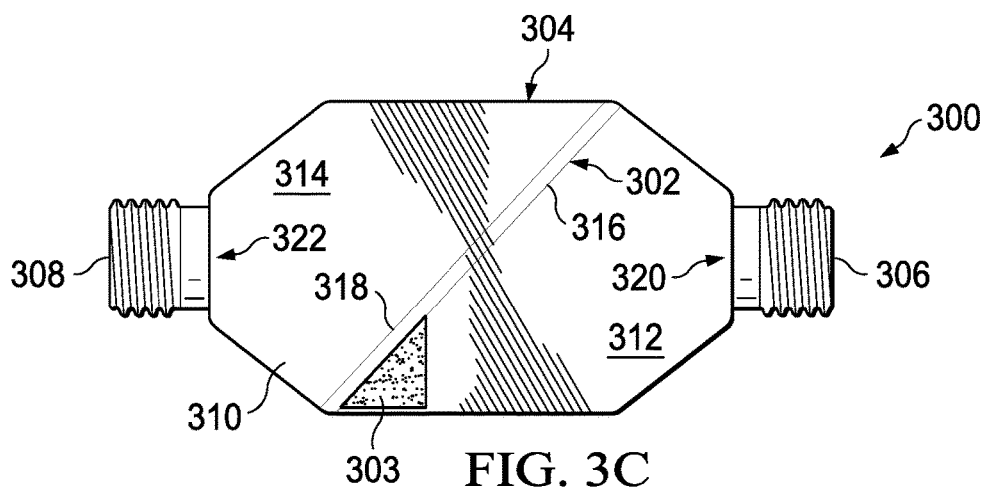

An exemplary integration of the closed system cell separation device 200 (without the housing) with external equipment is shown in FIGS. 2C-2D. In FIG. 2C, the cell separation device 200 in the beginning of the process is in-line and connected to an output of a spheroid perfusion bioreactor 260. The spheroid perfusion bioreactor 260 has an input connected to an output of an oxygenator 262. The oxygenator 262 has an input connected to the output of a pump 264. The pump 264 has an input which receives fresh liquid (e.g., fresh cell culture medium). There is also a controller 265 and a network 266 of waste flow pipes and valves connected to the output of the spheroid perfusion bioreactor 260 and the input of the pump 264. In this exemplary set-up, the cell separation device 200 remains in-line with the spheroid perfusion bioreactor 260 until the spheroids are removed from the spheroid perfusion bioreactor 260 and collected in the cell separation device 200. After the spheroids are collected in the cell separation device 200, the cell separation device 200 is disconnected from the spheroid perfusion bioreactor 260 and connected to a cell dissociation reagent container 270, a washing solution container 272 (e.g., PBS container 272), a waste container 274, and a cell collection container 276 as shown in FIG. 2D.

At this point, one can use the cell separation device 200 to obtain the cells from the spheroids located therein by performing the following exemplary steps:
1) Position the cell separation device 200 so the porous mesh 202 is almost in a horizontal orientation. Assume all of the clamps and valves shown in FIG. 2 are closed.
2) Open the clamp 267 and valve 236 from the PBS container 272 to the cell separation device 200. Plus, open the clamp 238 and the vent filter 240 which is associated with the cell separation device 200. The PBS will flow by gravity into the cell separation device 200 and any air in the cell separation device 200 will leave through the vent filter 240.
3) Close the PBS tubing clamp 267 and valve 236 after as much PBS as required enters the cell separation device 200.
4) Tilt the cell separation device 200 side-to-side to wash the spheroids in the collected PBS.
5) Open the valve 246 and clamps 269 and 271 from the cell separation device 200 to the waste container 274. Plus, open the clamp 273 (if present) and the vent filter 275 (if present) on the waste container 274.
6) Position the cell separation device 200 so the porous mesh 202 is substantially vertically orientated and let the PBS drain due to gravity to the waste container 274.
7) Close the clamp 271 to the waste container 274. Close the valve 246 associated with the cell separation device 200. Open clamp 277 and valve 236 on the path from the cell dissociation reagent container 270 to the cell separation device 200. The cell dissociation reagent will flow into the cell separation device 200 due to gravity.
8) Position the cell separation device 200 on a side so the porous mesh 202 is horizontal. Gently rock the cell separation device 200 to enable the cells to dissociate from the spheroids.
9) Once the cells have dissociated, vertically orient the cell separation device 200 so that the porous mesh 202 is substantially vertically orientated.
10) Open the valve 246 and clamps 269 and 279 to the cell collection container 276. Plus, open the clamp 281 (if present) to the vent filter 283 (if present) attached to the cell collection container 276. The dissociated cells will flow by gravity into the cell collection container 276.

Note: If the waste container 274 and cell collection container 276 are bags, then the vent filters 275 and 283 will be unnecessary because no air will be present inside the bags on the first use. In contrast, the vents 275 and 283 would be used for a hard-sided waste container 274 and a hard-side cell collection container 276 which have a defined geometry since air will be present in the containers 274 and 276 and needs to escape in order for the fluid to flow into the hard-sided waste container 274 and the hard-sided cell collection container 276.

It should be appreciated that the cell separation device 200 could be configured to be an open-system cell separation device 200 where the first flow control system 232 and the second flow control system 234 would be replaced with caps. Likewise, the cell separation device 100 could be configured to be a close-system cell separation device 100 where the caps 124 and 126 would be replaced with a first flow control system and second flow control system. This is true for all of the cell separation devices described herein.

Referring to FIG. 3A, there is a front view of a cell separation device 300 configured in accordance with an embodiment of the present disclosure. In this embodiment, the cell separation device 300 comprises a vessel 304 having a first port 306, a second port 308, and a cavity 310. The cell separation device 300 further comprises a porous mesh 302 disposed within the cavity 310 to divide the cavity 310 into a first compartment 312 and a second compartment 314. The first port 306 is in communication with the first compartment 312 of the cavity 310. Further, the first port 306 is located to a first side 316 of the porous mesh 302. The second port 308 is in communication with the second compartment 314 of the cavity 310. Further, the second port 308 is located to a second side 318 of the porous mesh 302. In addition, the first port 306 is located at one end 320 of the vessel 304 and the second port 308 is located at an opposing end 322 of the vessel 304. Also, the first port 306 and the second port 308 are in-line with one another on the vessel 304 such that the porous mesh 302 has the inclined orientation within the cavity 310 when (1) the first port 306 is located in a substantially upward orientation and the second port 308 is located in a substantially downward orientation (as shown in FIG. 3A), or (2) the first port 306 is located in the substantially downward orientation and the second port 308 is located in the substantially upward orientation. In this exemplary embodiment, the cell separation device 300 can also have a housing (not shown) that surrounds a large portion of the cell separation device 300 except for the first port 306 and the second port 308 (see FIG. 1A for an exemplary housing 130 that could be used with the cell separation device 300). If used, the housing would permit the rotation of the cell separation device 300 (which can have a flexible vessel 304) and in general aid in the handling of the cell separation device 300.

In this example, the cell separation device 300 is configured to be an open-system cell separation device 300 because it is not directly connected to external equipment such as a bioreactor, vacuum pump etc. . . . . . In this configuration, the cell separation device 300 has a first cap 324 that is attachable to the first port 306 (i.e., the first cap 324 can be secured to the first port 306 or removed from the first port 306). Further, the cell separation device 300 has a second cap 326 that is attachable to the second port 308 (i.e., the second cap 326 can be secured to the second port 308 or removed from the second port 308).

The following is a description on how the cell separation device 300 could be used to obtain cells from microcarriers. During this exemplary process, the cell separation device 300 should be located and manipulated within a biological hood to avoid contamination of the cells. There are two positions into which the cell separation device 300 could placed to obtain cells from microcarriers. In position 1, the cell separation device 300 is in a vertical orientation with the cap 324/first port 306 in an upward orientation and the cap 326/second port 308 in a downward orientation (see FIG. 3B). In position 2, the cell separation device 300 is in a horizontal orientation with the cap 324/first port 306 facing to the right and the cap 326/second port 308 facing to the left (see FIG. 3C). The following steps can be performed:
1) With the cell separation device 300 in position 1, remove the caps 324 and 326.
2) Place the lower end including the second port 308 of the cell separation device 300 into an empty waste collection vessel.
3) Pour the cell-covered microcarriers and medium from the culture vessel into the first port 124 of the cell separation device 300. The medium will flow through the porous mesh 302 in the cell separation device 300 and out the second port 108 into the waste collection vessel but the cell-covered microcarriers will be retained by the porous mesh 302 in the cell separation device 300. (The retained microcarriers are designated by the shaded triangle 303 in the image).
4) Lift the cell separation device 300 out of the waste collection vessel and place the cell separation device 300 in position 2 (horizontal orientation).
5) Add a volume of washing solution (e.g., PBS) and wash the cell-covered microcarriers by rocking the cell separation device 300 slightly side-to-side.
6) Hold the cell separation device 300 over the waste collection vessel and allow the PBS wash to exit the cell separation device 300 by holding it in position 1. Repeat the washing steps 4-6 if desired.
7) Place the cell separation device 300 in position 2 and add the cell dissociation reagent into the first port 306 to the cell separation device 300. Gently rock the cell separation device 300 side-to-side occasionally during the incubation period necessary to dissociate the cells from the microcarriers.
8) After the cells are dissociated from the microcarriers, collect the cells and dissociation reagent (e.g., trypsin) by placing the cell separation device 300 over a cell collection container in position 1.
9) Place the cell separation device 300 in position 2. Add a volume of cell collection solution (e.g., fresh culture medium) to the cell separation device 300 and gently rock the cell separation device 300 side-to-side to rinse the remaining cells off of the microcarriers.
10) Add the cell collection solution to the cells in the cell collection container by placing the cell separation device 300 in position 1. The microcarriers will be left in the cell separation device 300, and the cells will be in the cell collection container.

The following is a description on how the cell separation device 300 could be used to obtain cells from cell-spheroids. During this exemplary process, the cell separation device 300 should be located and manipulated within a biological hood to avoid contamination of the cells. There are two positions into which the cell separation device 300 could placed to remove cells from microcarriers. In position 1, the cell separation device 300 is in a vertical orientation with the cap 324/first port 306 in an upward orientation and the cap 326/second port 308 in a downward orientation (see FIG. 3B). In position 2, the cell separation device 300 is in a horizontal orientation with the cap 324/first port 306 facing to the right and the cap 326/second port 308 facing to the left (see FIG. 3C). The following steps can be performed:
1) With the cell separation device 300 in position 1, remove the caps 324 and 326.
2) Place the lower end including the second port 308 of the cell separation device 300 into an empty waste collection vessel.
3) Pour the cell-spheroids and medium from the culture vessel into the first port 306 of the cell separation device 300. The medium will flow through the porous mesh 302 of the cell separation device 300 and out the second port 308 into the waste collection vessel but the cell-spheroids will be retained in the cell separation device 300. (The retained spheroids are designated by the shaded triangle 303 in the image)
4) Lift the cell separation device 300 out of the waste vessel and place the cell separation device 300 in position 2 (horizontal orientation).
5) Add a volume of washing solution (e.g., PBS) and wash the cell-spheroids by rocking the cell separation device 300 slightly side-to-side.
6) Hold the cell separation device 300 over the waste collection vessel in position 1 and allow the PBS wash to exit the cell separation device 300. Repeat washing steps 4-6 if desired.
7) Place the cell separation device 300 in position 2 and add the cell dissociation reagent (e.g., trypsin) through the first port 306 into the cell separation device 300. Gently rock the cell separation device 300 side-to-side occasionally during the incubation period necessary to dissociate single cells from the spheroids. It may be necessary to put the cell separation device 300 into an incubator to fully dissociate the cells from the spheroids. If so, recap the cell separation device 300 before moving the cell separation device 300 out of the hood.
8) After the cells form a single cell suspension, collect the cells and dissociation reagent by placing the cell separation device 300 and in particular the second port 308 over a cell collection container in position 1. The cell separation device 300 should be devoid of cells following this step.

Figure 4A:
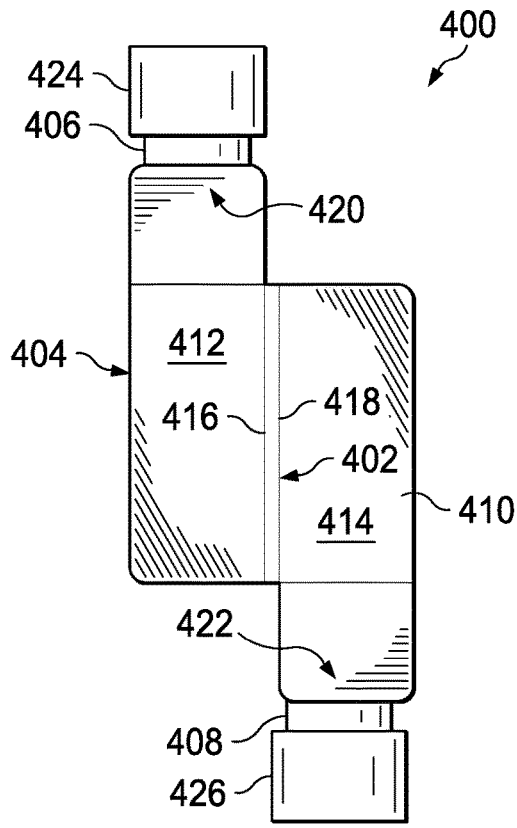
FIGS. 4A-4C illustrate a cell separation device configured in accordance with an embodiment of the present disclosure.
Figure 4B:
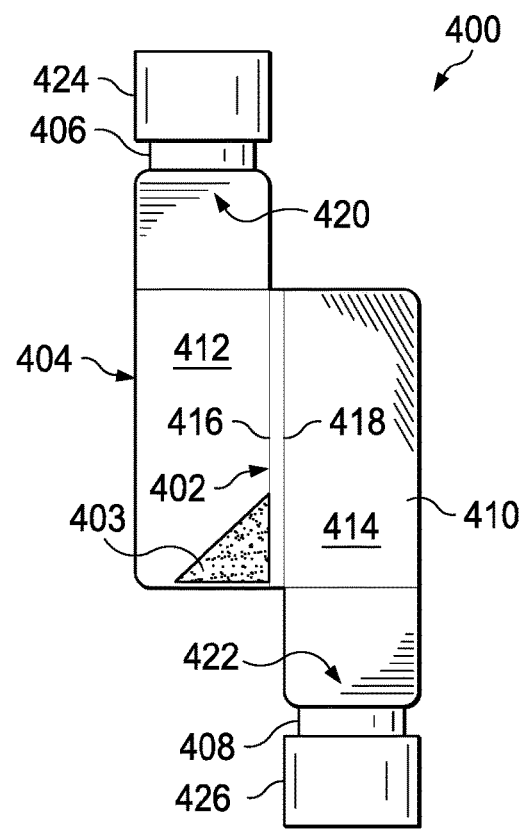
Figure 4C:
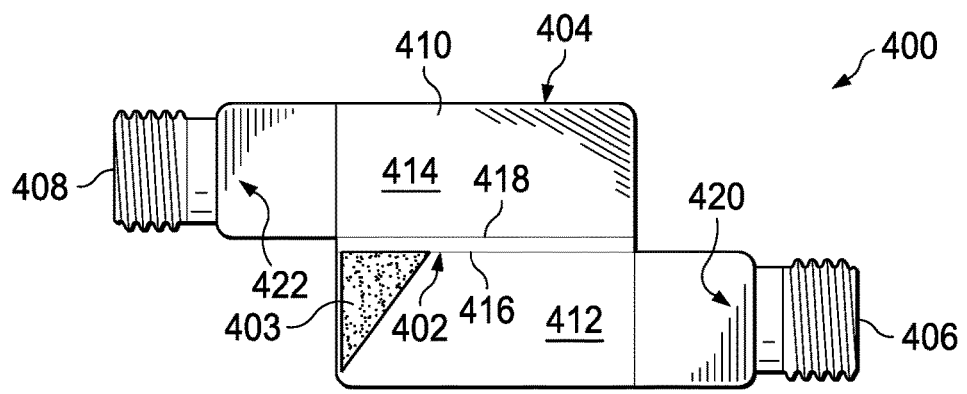

Referring to FIG. 4A, there is illustrated a front view of a cell separation device 400 configured in accordance with an embodiment of the present disclosure. As shown, the cell separation device 400 comprises a vessel 404 having a first port 406, a second port 408, and a cavity 410. The cell separation device 400 further comprises the porous mesh 402 disposed within the cavity 410 so as to divide the cavity 410 into a first compartment 412 and a second compartment 414. The first port 406 is in communication with the first compartment 412 of the cavity 410. Further, the first port 406 is located to a first side 416 of the porous mesh 402. The second port 408 is in communication with the second compartment 414 of the cavity 410. Further, the second port 408 is located to a second side 418 of the porous mesh 402. In addition, the first port 406 is located at one end 420 of the vessel 404 and the second port 408 is located at an opposing end 422 of the vessel 404. Also, the first port 406 and the second port 408 are off-set from one another on the vessel 404 such that the porous mesh 402 has the substantially vertical orientation within the cavity 110 when (1) the first port 406 is located in a substantially upward orientation and the second port 408 is located in a substantially downward orientation (as shown in FIG. 4A), or (2) the first port 406 is located in the substantially downward orientation and the second port 408 is located in the substantially upward orientation. In this exemplary embodiment, the cell separation device 400 can also have a housing (not shown) that surrounds a large portion of the cell separation device 400 except for the first port 406 and the second port 408 (see FIG. 1A for an exemplary housing 130 that could be used with the cell separation device 400). If used, the housing would permit the rotation of the cell separation device 400 (which can have a flexible vessel 404) and in general aid in the handling of the cell separation device 400.

In this example, the cell separation device 400 is configured to be an open-system cell separation device 400 because it is not directly connected to external equipment such as a bioreactor, vacuum pump etc. . . . . . In this configuration, the cell separation device 400 has a first cap 424 that is attachable to the first port 406 (i.e., the first cap 424 can be secured to the first port 406 or removed from the first port 406). Further, the cell separation device 400 has a second cap 426 that is attachable to the second port 408 (i.e., the second cap 426 can be secured to the second port 408 or removed from the second port 408).

The following is a description on how the cell separation device 400 could be used to obtain cells from microcarriers. During this exemplary process, the cell separation device 400 should be located and manipulated within a biological hood to avoid contamination of the cells. There are two positions into which the cell separation device 400 could placed to remove cells from microcarriers. In position 1, the cell separation device 400 is in a vertical orientation with the cap 424/first port 406 in an upward orientation and the cap 426/second port 408 in a downward orientation (see FIG. 4B). In position 2, the cell separation device 400 is in a horizontal orientation with the cap 424/first port 406 facing to the right and the cap 426/second port 408 facing to the left (see FIG. 4C). The following steps can be performed:

1) With the cell separation device 400 in position 1, remove the caps 424 and 426.
2) Place the lower end including the second port 408 of the cell separation device 400 into an empty waste collection vessel.
3) Pour the cell-covered microcarriers and medium from the culture vessel into the first port 424 of the cell separation device 400. The medium will flow through the porous mesh 402 in the cell separation device 400 and out the second port 108 into the waste collection vessel but the cell-covered microcarriers will be retained by the porous mesh 402 in the cell separation device 400. (The retained microcarriers are designated by the shaded triangle 403 in the image).
4) Lift the cell separation device 400 out of the waste vessel and place the cell separation device 400 in position 2 (horizontal orientation).
5) Add a volume of washing solution (e.g., PBS) and wash the cell-covered microcarriers by rocking the cell separation device 400 slightly side-to-side.
6) Hold the cell separation device 400 over the waste vessel and allow the PBS wash to exit the cell separation device 400 by holding it in position 1. Repeat the washing steps 4-6 if desired.
7) Place the cell separation device 400 in position 2 and add the cell dissociation reagent (e.g., trypsin) into the first port 406 to the cell separation device 400. Gently rock the cell separation device 400 side-to-side occasionally during the incubation period necessary to dissociate the cells from the microcarriers.
8) After the cells are dissociated from the microcarriers, collect the cells and the cell dissociation reagent by placing the cell separation device 400 over a sterile container in position 1.
9) Place the cell separation device 400 in position 2. Add a volume of cell collection solution (e.g., fresh culture medium) to the cell separation device 400 and gently rock the cell separation device 400 side-to-side to rinse the remaining cells off of the microcarriers.
10) Add the cell collection solution to the cells in the cell collection container by placing the cell separation device 400 in position 1. The microcarriers will be left in the cell separation device 400, and the cells will be in the cell collection container.

The following is a description on how the cell separation device 400 could be used to obtain cells from cell-spheroids. During this exemplary process, the cell separation device 400 should be located and manipulated within a biological hood to avoid contamination of the cells. There are two positions into which the cell separation device 400 could placed to remove cells from microcarriers. In position 1, the cell separation device 400 is in a vertical orientation with the cap 424/first port 406 in an upward orientation and the cap 426/second port 408 is a downward orientation (see FIG. 4B). In position 2, the cell separation device 400 is in a horizontal orientation with the cap 424/first port 406 facing to the right and the cap 426/second port 408 facing to the left (see FIG. 4C). The following steps can be performed:

1) With the cell separation device 400 in position 1, remove the caps 424 and 426.
2) Place the lower end including the second port 408 of the cell separation device 400 into an empty waste collection vessel.
3) Pour the cell-spheroids and medium from the culture vessel into the first port 406 of the cell separation device 400. The medium will flow through the porous mesh 402 of the cell separation device 400 and out the second port 408 into the waste collection vessel but the cell-spheroids will be retained in the cell separation device 400. (The retained spheroids are designated by the shaded triangle 403 in the image)
4) Lift the cell separation device 400 out of the waste vessel and place the cell separation device 400 in position 2 (horizontal orientation).
5) Add a volume of washing solution (e.g., PBS) and wash the cell-spheroids by rocking the cell separation device 400 slightly side-to-side.
6) Hold the cell separation device 400 over the waste vessel in position 1 and allow the PBS wash to exit the cell separation device 400. Repeat washing steps 4-6 if desired.
7) Place the cell separation device 400 in position 2 and add the cell dissociation reagent (e.g., trypsin) through the first port 406 into the cell separation device 400. Gently rock the cell separation device 400 side-to-side occasionally during the incubation period necessary to dissociate single cells from the spheroids. It may be necessary to put the cell separation device 400 into an incubator to fully dissociate the cells from the spheroids. If so, recap the cell separation device 400 before moving the cell separation device 400 out of the hood.

8) After the cells form a single cell suspension, collect the cells and the cell dissociation reagent by placing the cell separation device 400 and in particular the second port 408 over a sterile cell collection container in position 1. The cell separation device 400 should be devoid of cells following this step.

Figure 5A:
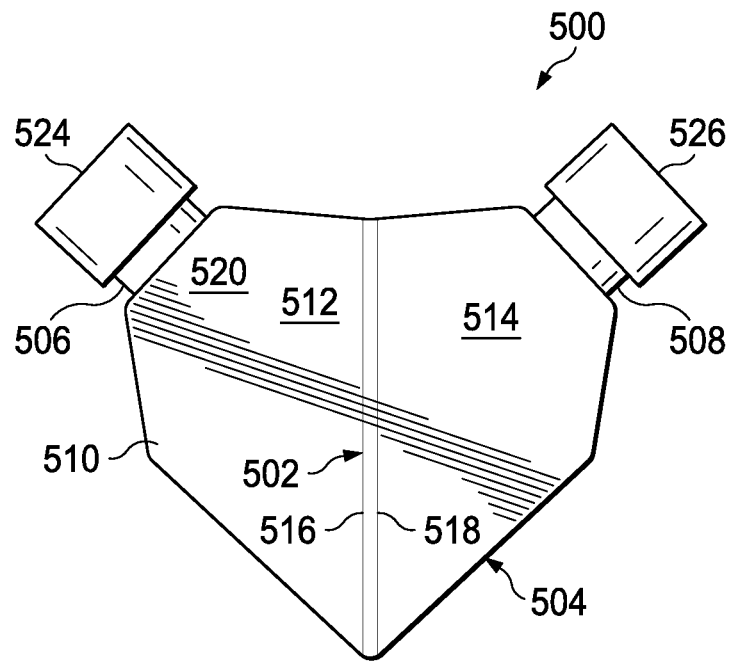
FIGS. 5A-5D illustrate a cell separation device configured in accordance with an embodiment of the present disclosure.
Figure 5B:
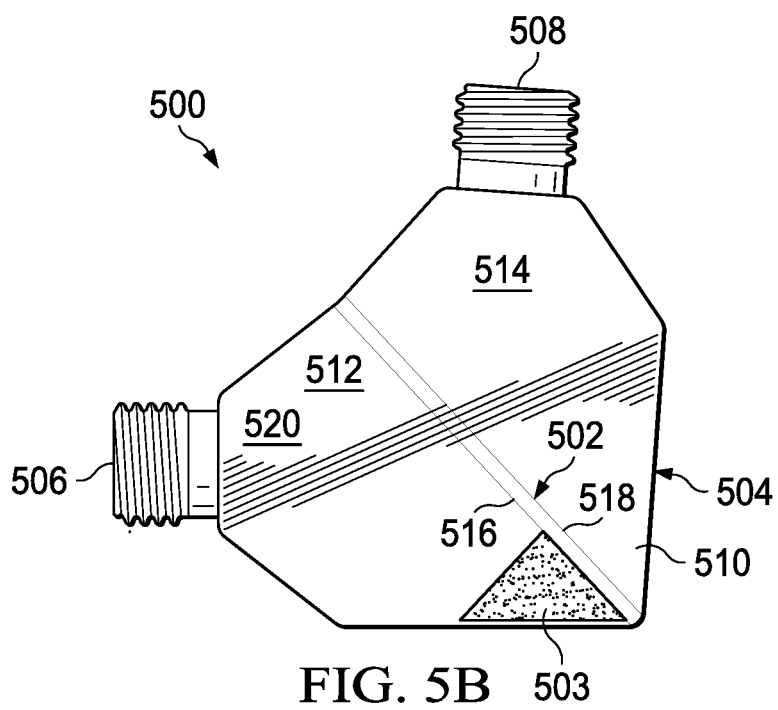
Figure 5C:
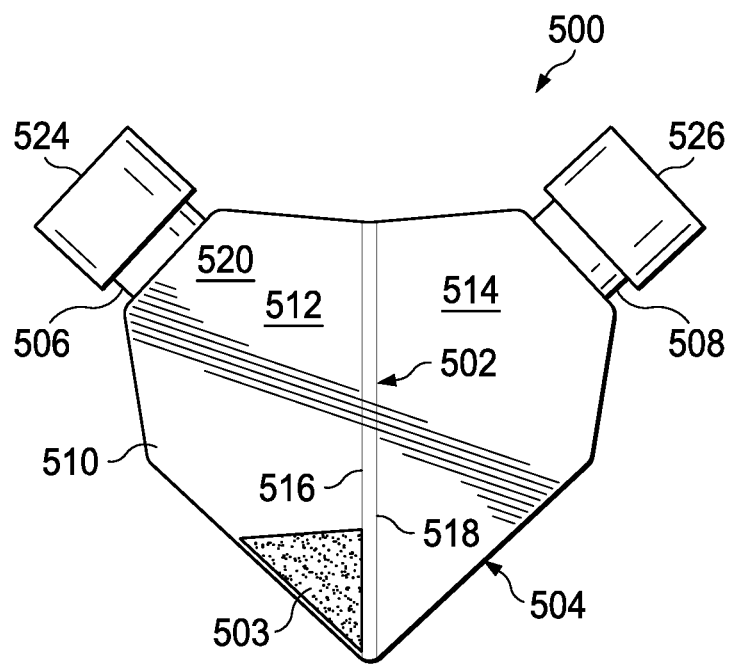
Figure 5D:
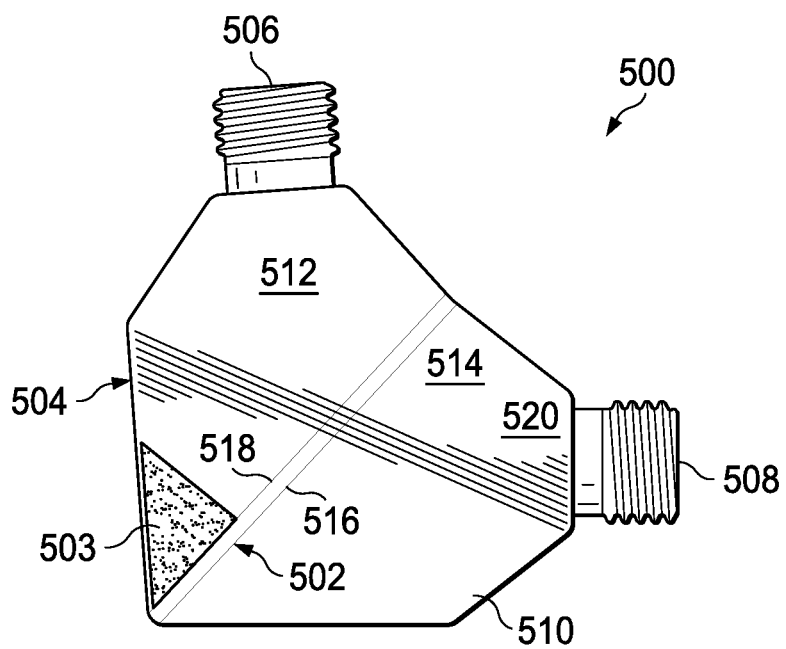

Referring to FIG. 5A, there is illustrated a front view of a cell separation device 500 configured in accordance with an embodiment of the present disclosure. As shown, the cell separation device 500 comprises a vessel 504 having a first port 506, a second port 508, and a cavity 510. The cell separation device 500 further comprises the porous mesh 502 disposed within the cavity 510 so as to divide the cavity 510 into a first compartment 512 and a second compartment 514. The first port 506 is in communication with the first compartment 512 of the cavity 510. Further, the first port 506 is located to a first side 516 of the porous mesh 502. The second port 508 is in communication with the second compartment 514 of the cavity 510. Further, the second port 508 is located to a second side 518 of the porous mesh 502. In addition, the first port 506 and the second port 508 are both located on one side 520 of the vessel 504 such that the porous mesh 502 has a substantially vertical orientation within the cavity 510 when (1) the first port 506 and the second port 508 are located in a substantially upward orientation (shown in FIG. 5A), or (2) the first port 506 and the second port 508 are located in a substantially downward orientation (not shown). In this exemplary embodiment, the cell separation device 500 can also have a housing (not shown) that surrounds a large portion of the cell separation device 500 except for the first port 506 and the second port 508. If used, the housing would permit the rotation of the cell separation device 500 (which can have a flexible vessel 504) and in general aid in the handling of the cell separation device 500.

In this example, the cell separation device 500 is configured to be an open-system cell separation device 500 because it is not directly connected to external equipment such as a bioreactor, vacuum pump etc. . . . . In this configuration, the cell separation device 500 has a first cap 524 that is attachable to the first port 506 (i.e., the first cap 524 can be secured to the first port 506 or removed from the first port 506). Further, the cell separation device 500 has a second cap 526 that is attachable to the second port 508 (i.e., the second cap 526 can be secured to the second port 508 or removed from the second port 508).

The following is a description on how the cell separation device 500 could be used to obtain cells from microcarriers. During this exemplary process, the cell separation device 500 should be located and manipulated within a biological hood to avoid contamination of the cells. There are three positions into which the cell separation device 500 could placed to remove cells from microcarriers. In position 1, the cell separation device 500 is positioned with the cap 524/first port 506 to the left and the other cap 526/second port 508 upright (see FIG. 5B). In position 2, both caps 524 and 526/ports 506 and 508 of the cell separation device 500 are angled upright (see FIG. 5C). In position 3, the cap 526/second port 508 is to the right and the other cap 524/first port is upright (see FIG. 5D). The following steps can be performed:

1) With the cell separation device 500 in position 2, remove the caps 524 and 526.

2) Pour the cell-covered microcarriers and medium from the culture vessel into the first port 506 of the cell separation device 500.

3) Set a waste collection container on the right, and tip the cell separation device 500 into position 3 to empty the waste medium from the second port 508 of the cell separation device 500 into the waste container. The medium will flow through the porous mesh 502 of the cell separation device 500 and through the second port 508 into the waste collection vessel but the cell-covered microcarriers will be retained in the cell separation device 500. (The retained cell-covered microcarriers are designated by the shaded triangle 503 in the image)

4) Tip the cell separation device 500 to position 2 again and add a volume of washing solution (e.g., PBS) into the first port 506.

5) Wash the cell-covered microcarriers by rocking the cell separation device 500 slightly side-to-side.

6) Hold the cell separation device 500 over the waste vessel in position 3 and allow the PBS wash to exit from the second port 508 of the cell separation device 500. Repeat the washing steps 4-6 if desired.

7) Place the cell separation device 500 in position 1 and add a cell dissociation reagent (e.g., trypsin) through the first port 506 into the cell separation device 500. Gently tip the cell separation device 500 side-to-side occasionally during the incubation period necessary to dissociate the cells from the microcarriers. It may be necessary to put the cell separation device 500 into an incubator to fully dissociate the cells. If so, recap the cell separation device 500 before moving the cell separation device 500 out of the hood and place it in position 1 during incubation.

8) After the all the cells are dissociated from the microcarriers, collect the cells and the cell dissociation reagent by placing the second port 508 of the cell separation device 500 over a sterile cell collection container in position 3.

9) Place the cell separation device 500 in position 2. Add a volume of cell collection solution (e.g., fresh culture medium) to the cell separation device 500 and gently rock the cell separation device 500 side-to-side to rinse the remaining cells off of the microcarriers.

10) Add the cell collection solution to the cells in the sterile cell collection container by placing the cell separation device 500 in position 3. The microcarriers will be left in the cell separation device 500, and the cells will be in the sterile cell collection container.

The following is a description on how the cell separation device 500 could be used to obtain cells from cell-spheroids. During this exemplary process, the cell separation device 500 should be located and manipulated within a biological hood to avoid contamination of the cells. There are three positions into which the cell separation device 500 could placed to remove cells from microcarriers. In position 1, the cell separation device 500 is positioned with the cap 524/first port 506 to the left and the other cap 526/second port 508 upright (see FIG. 5B). In position 2, both caps 524 and 526 (ports 506 and 508) of the cell separation device 500 are angled upright (see FIG. 5C). In position 3, the cap 526/second port 508 is to the right and the other cap 524/first port 506 is upright (see FIG. 5D). The following steps can be performed:

1) With the cell separation device 500 in position 2, remove the caps 524 and 526.

2) Pour the cell-spheroids and medium from the culture vessel into the first port 506 of the cell separation device 500.

3) Set a waste collection container on the right, and tip the cell separation device 500 into position 3 to empty the waste medium that passed through the porous mesh 502 of the cell separation device 500 and the second port 508 into the waste container. The medium will flow through the cell separation device 500 into the waste collection vessel but the cell-spheroids will be retained in the cell separation device 500. (The retained spheroids are designated by the shaded triangle 503 in the image)

4) Tip the cell separation device 500 to position 2 again and add a volume of washing solution (e.g., PBS) into the first port 506.

5) Wash the cell-spheroids by rocking the cell separation device 500 slightly side-to-side.

6) Hold the cell separation device 500 over the waste vessel in position 3 and allow the PBS wash to exit the cell separation device 500 through the second port 508. Repeat the washing steps 4-6 if desired.

7) Place the cell separation device 500 in position 1 and add a cell dissociation reagent (e.g., trypsin) to the first port 506 of the cell separation device 500. Gently tip the cell separation device 500 side-to-side occasionally during the incubation period necessary to dissociate single cells from the spheroid. It may be necessary to put the cell separation device 500 into an incubator to fully dissociate the cells. If so, recap the cell separation device 500 before moving the cell separation device 500 out of the hood and place it in position 1.

8) After the cells form a single cell suspension, collect the cells and the cell dissociation reagent by placing the second port 508 of the cell separation device 500 over a sterile cell collection container in position 3. The cell separation device 500 should be devoid of cells following this step.

Figure 6A:
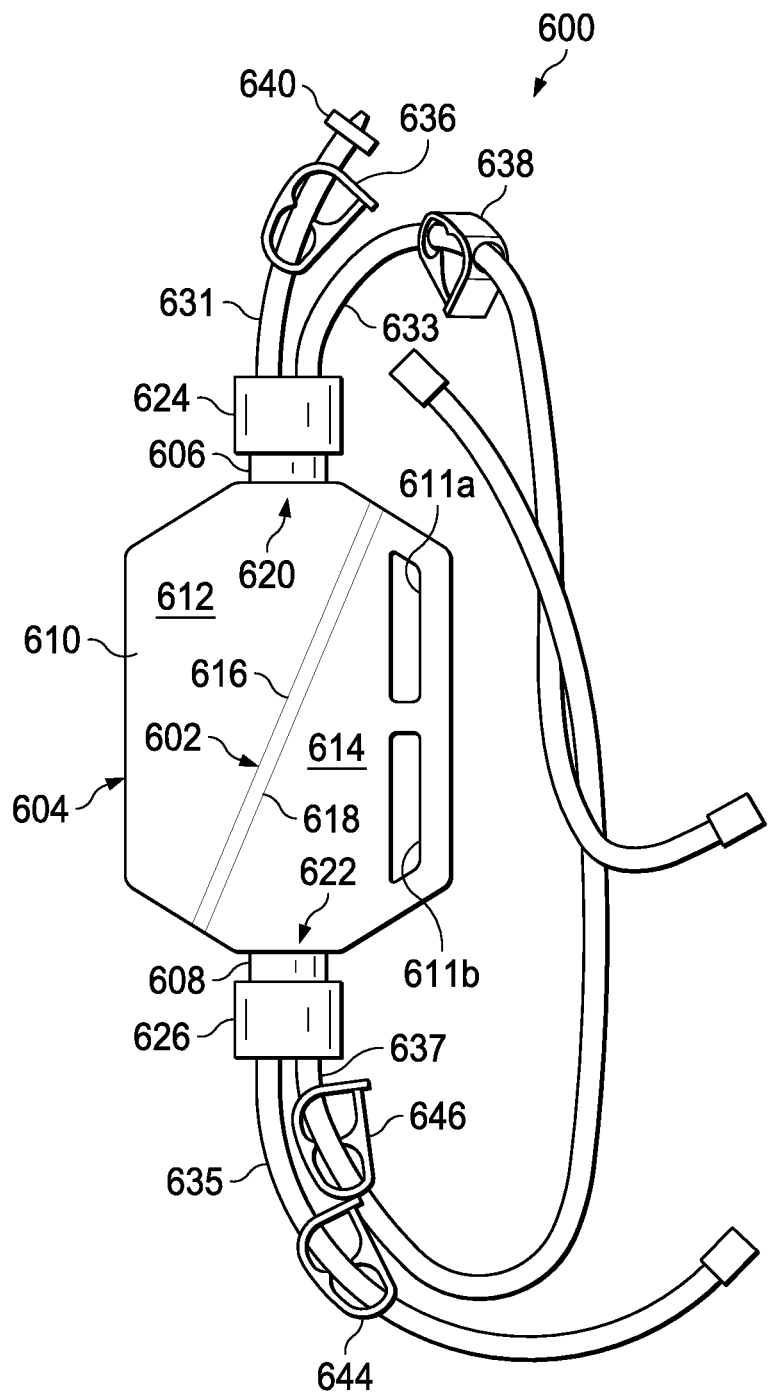
FIG. 6A illustrates a cell separation device configured in accordance with an embodiment of the present disclosure.

Referring to FIG. 6A, there is illustrated a front view of a cell separation device 600 configured in accordance with an embodiment of the present disclosure. In this embodiment, the cell separation device 600 comprises a vessel 604 having a first port 606, a second port 608, and a cavity 610. The cell separation device 600 further comprises a porous mesh 602 disposed within the cavity 610 to divide the cavity 610 into a first compartment 612 and a second compartment 614. The first port 606 is in communication with the first compartment 612 of the cavity 610. Further, the first port 606 is located to a first side 616 of the porous mesh 602. The second port 608 is in communication with the second compartment 614 of the cavity 610. Further, the second port 608 is located to a second side 618 of the porous mesh 602. In addition, the first port 606 is located at one end 620 of the vessel 604 and the second port 608 is located at an opposing end 622 of the vessel 604. Also, the first port 606 and the second port 608 are in-line with one another on the vessel 604 such that the porous mesh 602 has the inclined orientation within the cavity 610 when (1) the first port 606 is located in a substantially upward orientation and the second port 608 is located in a substantially downward orientation (as shown in FIG. 6A), or (2) the first port 606 is located in the substantially downward orientation and the second port 608 is located in the substantially upward orientation. The cell separation device 600 further has openings 611a and 611b formed in the vessel 604 to aid in the handling of the cell separation device 600. In this exemplary embodiment, the cell separation device 600 can also have a housing (not shown) that surrounds a large portion of the cell separation device 600 except for the first port 606 and the second port 608 (see FIG. 1A for an exemplary housing 130 that could be used with the cell separation device 600). If used, the housing would permit the rotation of the cell separation device 600 (which can have a flexible vessel 604) and in general aid in the handling of the cell separation device 600.

In this example, the cell separation device 600 is configured to be a closed-system cell separation device 600 because it is directly connected to external equipment such as a bioreactor, vacuum pump etc. . . . as discussed in more detail next with respect to FIG. 6B. In the exemplary configuration shown, the cell separation device 600 has a first cap 624 that is attachable to the first port 606 (i.e., the first cap 624 can be secured to the first port 606 or removed from the first port 606). Further, the cell separation device 600 has a second cap 626 that is attachable to the second port 608 (i.e., the second cap 626 can be secured to the second port 608 or removed from the second port 608). In the illustrated example, the first cap 624 is configured to receive (1) a first tube 631 which has a clamp 636 connected thereto and a vent filter 640 attached to another end thereof and (2) a second tube 633 having a clamp 638 connected thereto and another end connected to external equipment as shown for example in FIG. 6B, Likewise, the second cap 626 is configured to receive (1) a first tube 635 which has a clamp 644 connected thereto and another end connected to external equipment as shown for example in FIG. 6B, and (2) a second tube 637 which has a clamp 646 connected thereto and another end connected to external equipment as shown for example in FIG. 6B.

Figure 6B:
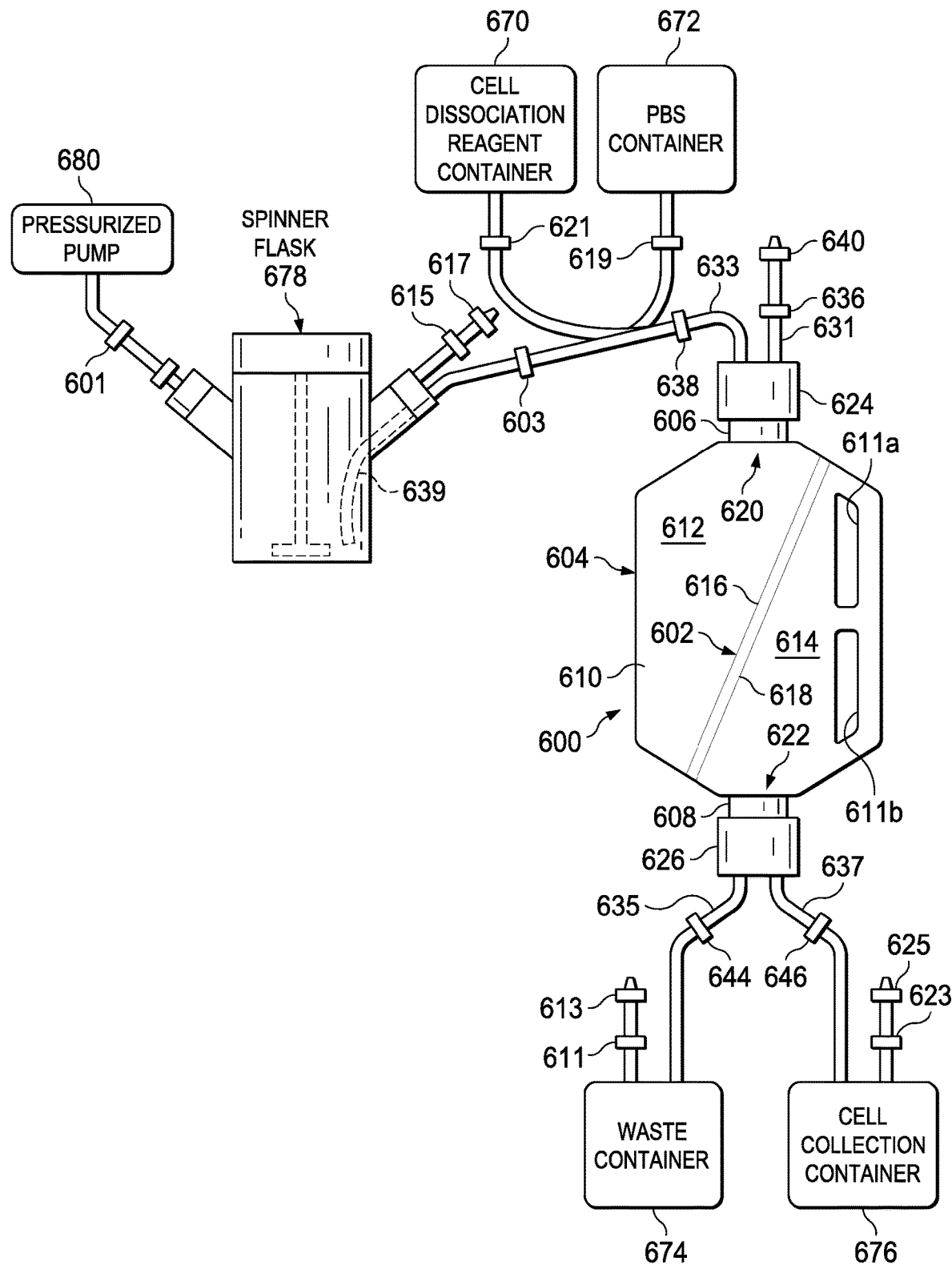
FIG. 6B illustrates an external system coupled to the cell separation device shown in FIG. 6A in accordance with an embodiment of the present disclosure.

An exemplary integration of the closed system cell separation device 600 (without the housing) with external equipment is shown in FIG. 6B. As shown in FIG. 6B, the cell separation device 600 is connected via a network of tubing and clamps to a cell dissociation reagent container 670, a washing solution container 672 (e.g., Phosphate Buffered Solution (PBS) container 672), a waste container 674, a cell collection container 676, a spinner flask 678 (which contains cell-covered microcarriers in a liquid), and a pressurized pump 680. The cell separation device 600 can be used to obtain the cells from microcarriers by performing the following steps:

1) Cells grow on microcarriers in the spinner flask 678 and need to be collected and dissociated from the microcarriers as discussed below.

2) Open the tubing clamp 601 at the pressurization pump 680 and the tubing clamps 603, 644, and 638 from the spinner flask 678 to the cell separation device 600 to the waste container 674. All other clamps remain or are closed.

3) Turn-on the pressurization pump 680. The cells, microcarriers and culture media will be forced up the dip-tube 639 and flow from the spinner flask 678 to the cell separation device 600 where the cell separation device 600 mesh will stop the cell-covered microcarriers while the culture media flows through to the waste container 674. The waster container 674 may have a clamp 611 which is opened at this time and connected via tubing to a vent filter 613.

4) Turn-off the pressurization pump 680 and open the clamp 615 to the vent filter 617 associated with the spinner flask 678, as well as opening the tubing clamps 603 and 619 along the fluid pathway from the PBS container 672 to the spinner flask 678. Other clamps are closed. The PBS flows into the spinner flask 678 by gravity through tubing.

5) Swirl the spinner flask 678 to re-suspend any remaining cell-covered microcarriers.

6) Close clamps 611, 615 on the vent filters 613 and 617 and open clamps 603 and 638 for the pathway from the spinner flask 678 to the cell separation device 600. Other clamps are closed.

7) Open clamp 601 and turn-on the pressurization pump 680 to initiate flow from the spinner flask 678 to the cell separation device 600. The PBS and cell-covered microcarriers will flow out of the spinner flask 678 to the cell separation device 600.

8) Turn-off the pressurization pump 680 and open the clamp 636 to the vent filter 640 on the cell separation device 600. Position the cell separation device 600 so the caps 624 and 626 are horizontal and tilt the cell separation device 600 side-to-side to wash the microcarriers in the collected PBS.

9) Open the clamp 644 to the waste container 674, position the cell separation device 600 vertically so cap 624 is up and cap 626 is down and let the PBS drain (by gravity) to the waste container 674.

10) Close the clamps 603, 644, and 619, and open clamps 621 and 638 on the path from the cell dissociation reagent container 670 to the cell separation device 600. The cell dissociation reagent will flow into the cell separation device 600 by gravity. Close the vent clamp 636.

11) Position the cell separation device 600 on a side so the caps 624 and 626 are horizontal. Gently rock the cell separation device 600 to enable the cells to dissociate from the microcarriers.

12) Vertically orient the cell separation device 600 so that cap 624 is up and cap 626 is down. Open the clamp 623 to vent filter 625 and the clamp 646 to the cell collection container 676. The dissociated cells will flow by gravity to the cell collection container 676 leaving the microcarriers behind in the cell separation device 600.

Figure 7A:
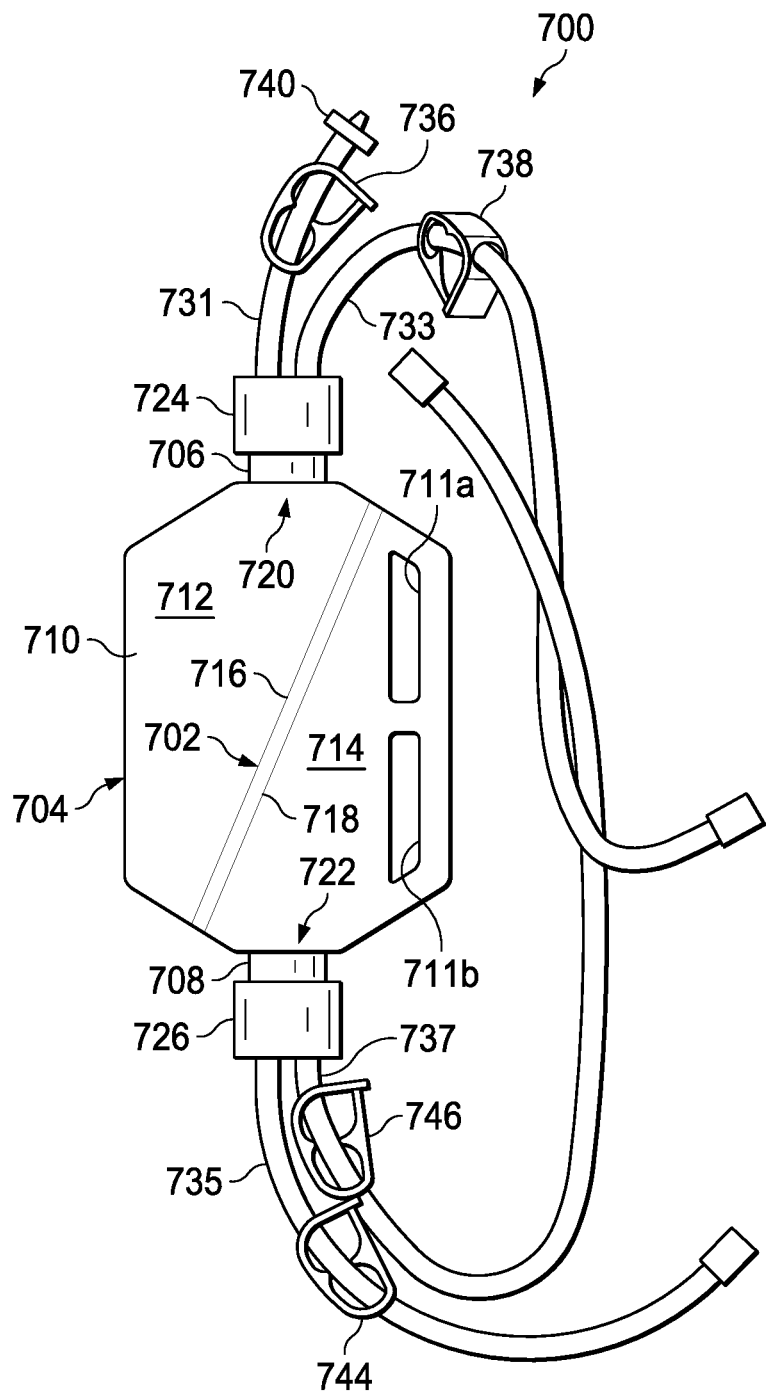
FIG. 7A illustrates a cell separation device configured in accordance with an embodiment of the present disclosure.

Referring to FIG. 7A, there is illustrated a front view of a cell separation device 700 configured in accordance with an embodiment of the present disclosure. In this embodiment, the cell separation device 700 comprises a vessel 704 having a first port 706, a second port 708, and a cavity 710. The cell separation device 700 further comprises a porous mesh 702 disposed within the cavity 710 to divide the cavity 710 into a first compartment 712 and a second compartment 714. The first port 706 is in communication with the first compartment 712 of the cavity 710. Further, the first port 706 is located to a first side 716 of the porous mesh 702. The second port 708 is in communication with the second compartment 714 of the cavity 710. Further, the second port 708 is located to a second side 718 of the porous mesh 702. In addition, the first port 706 is located at one end 720 of the vessel 704 and the second port 708 is located at an opposing end 722 of the vessel 704. Also, the first port 706 and the second port 708 are in-line with one another on the vessel 704 such that the porous mesh 702 has the inclined orientation within the cavity 710 when (1) the first port 706 is located in a substantially upward orientation and the second port 708 is located in a substantially downward orientation (as shown in FIG. 7A), or (2) the first port 706 is located in the substantially downward orientation and the second port 708 is located in the substantially upward orientation. The cell separation device 700 further has openings 711a and 711b formed in the vessel 704 to aid in the handling of the cell separation device 700. In this exemplary embodiment, the cell separation device 700 can also have a housing (not shown) that surrounds a large portion of the cell separation device 700 except for the first port 706 and the second port 708 (see FIG. 1A for an exemplary housing 130 that could be used with the cell separation device 700). If used, the housing would permit the rotation of the cell separation device 700 (which can have a flexible vessel 704) and in general aid in the handling of the cell separation device 700.

In this example, the cell separation device 700 is configured to be a closed-system cell separation device 700 because it is directly connected to external equipment such as a bioreactor, vacuum pump etc. . . . as discussed in more detail next with respect to FIG. 7B. In the exemplary configuration shown, the cell separation device 700 has a first cap 724 that is attachable to the first port 706 (i.e., the first cap 724 can be secured to the first port 706 or removed from the first port 706). Further, the cell separation device 700 has a second cap 726 that is attachable to the second port 708 (i.e., the second cap 726 can be secured to the second port 708 or removed from the second port 708). In the illustrated example, the first cap 724 is configured to receive (1) a first tube 731 which has a clamp 736 connected thereto and a vent filter 740 attached to another end thereof and (2) a second tube 733 having a clamp 738 connected thereto and another end connected to external equipment as shown for example in FIG. 7B, Likewise, the second cap 726 is configured to receive (1) a first tube 735 which has a clamp 744 connected thereto and another end connected to external equipment as shown for example in FIG. 7B, and (2) a second tube 737 which has a clamp 746 connected thereto and another end connected to external equipment as shown for example in FIG. 7B.

Figure 7B:
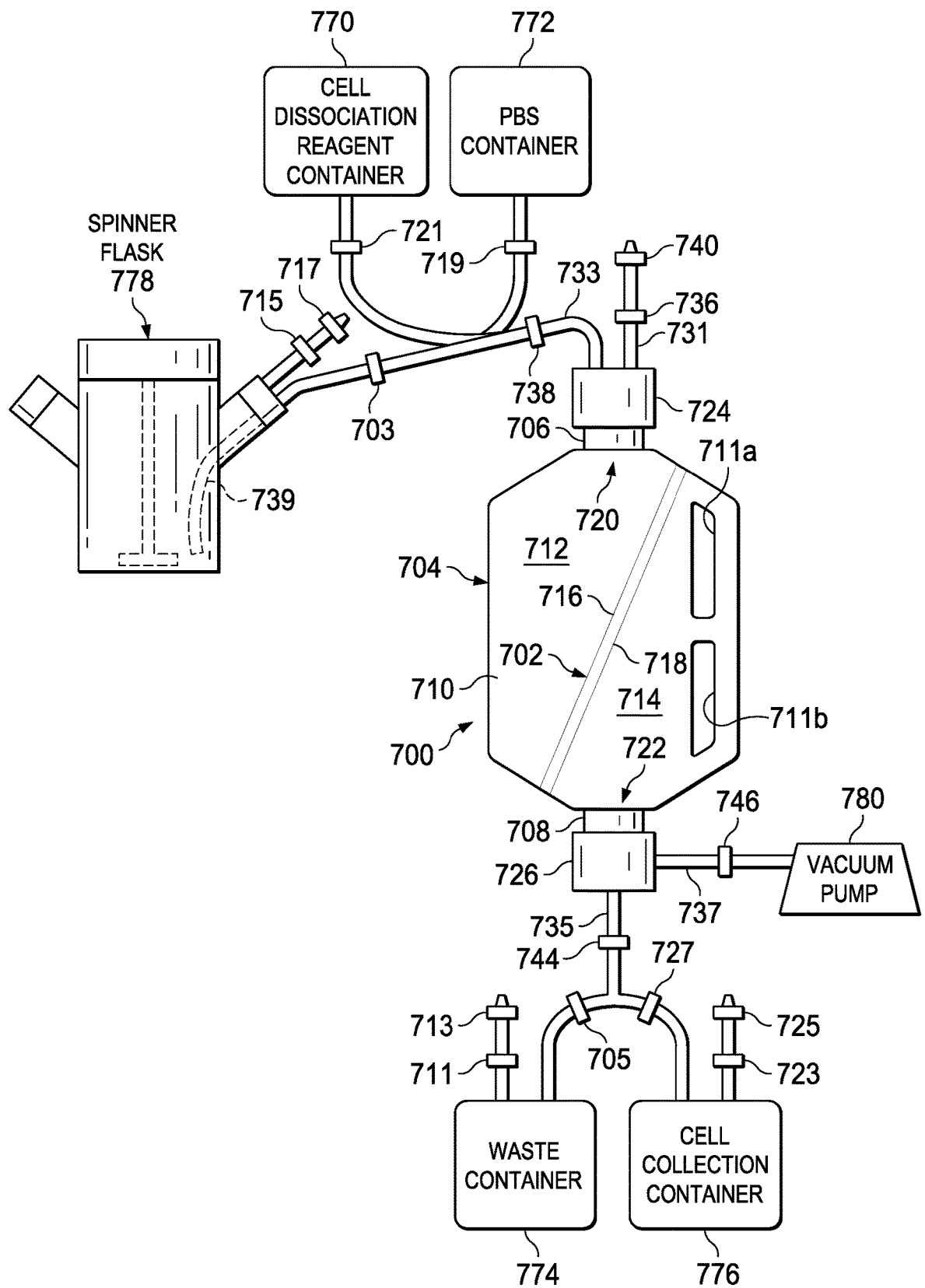
FIG. 7B illustrates an external system coupled to the cell separation device shown in FIG. 7A in accordance with an embodiment of the present disclosure; and, FIG. 8 is a flowchart illustrating the basic steps of a method for using the cell separation device shown in FIGS. 1-7 to obtain cells from microcarriers or spheroids in a liquid in accordance with an embodiment of the present disclosure.

An exemplary integration of the closed system cell separation device 700 (without the housing) with external equipment is shown in FIG. 7B. As shown in FIG. 7B, the cell separation device 700 is connected via a network of tubing and clamps to a cell dissociation reagent container 770, a washing solution container 772 (e.g., Phosphate Buffered Solution (PBS) container 772), a waste container 774, a cell collection container 776, a spinner flask 778 (which contains spheroids in a liquid), and a vacuum pump 780. The cell separation device 700 can be used to obtain the cells from spheroids by performing the following steps:

1) Open the tubing clamps 703, 705, 738 and 744 on the fluid path from the spinner flask 778 to the cell separation device 700 to the waste container 774. All other clamps are or remain closed.

2) Open clamp 746 and turn-on the vacuum pump 780. Spheroids and culture media will be pulled up the dip-tube 739 and flow through from the spinner flask 778 to the cell separation device 700 where the porous mesh 702 will stop the spheroids, while the culture media flows through to the waste container 774. The waster container 774 may have a clamp 711 which is opened at this time and connected via tubing to a vent filter 713.

3) Turn-off the vacuum pump 780 and then open the clamp 715 to the vent filter 717 associated with the spinner flask 778, as well as opening the tubing clamps 703 and 719 along the fluid pathway from the PBS container 772 to the spinner flask 778. Other clamps are closed. The PBS flows into the spinner flask 778 by gravity through tubing.

4) Swirl the spinner flask 778 to re-suspend any remaining spheroids.

5) Close clamps 711, 715 on the vent filters 713 and 717 and open clamps 703 and 738 for the pathway from the spinner flask 778 to the cell separation device 700. Other clamps are closed.

6) Open claim 746 and turn-on the vacuum pump 780 to initiate flow from the spinner flask 778 to the cell separation device 700. The PBS and spheroids will flow out of the spinner flask 778 to the cell separation device 700.

7) Turn-off the vacuum pump 780 and open the clamp 736 to the vent filter 740 on the cell separation device 700. Position the cell separation device 700 so the caps 724 and 726 are horizontal and tilt the cell separation device 700 side-to-side to wash the spheroids in the collected PBS.

8) Open the clamps 705 and 744 to the waste container 774, position the cell separation device 700 vertically so cap 724 is up and cap 726 is down and let the PBS drain (by gravity) to the waste container 774.

9) Close the clamps 703, 705, 719 and 744, and open clamps 721 and 738 on the path from the cell dissociation reagent container 770 to the cell separation device 700. The cell dissociation reagent will flow into the cell separation device 700 by gravity. Close the vent clamp 736.

10) Position the cell separation device 700 on a side so the caps 724 and 726 are horizontal. Gently rock the cell separation device 700 to enable the cells to dissociate from the spheroids.

11) Vertically orient the cell separation device 700 so that cap 724 is up and cap 726 is down. Open the clamp 723 to vent filter 725 and the clamp 727 to the cell collection container 776. The dissociated cells will flow by gravity from the cell separation device 700 to the cell collection container 776

In view of the descriptions associated with FIGS. 6A-6B and 7A-7B, it should be appreciated that there are several methods that can be used with the "closed-system" cell separation device 600 and 700, depending on the vessel used to culture the cells and whether pressurization or vacuum is the preferred method to move fluid throughout the system. It should also be appreciated that any of the aforementioned cell separation devices 100, 200, 300, 400, 500, 600 and 700 or equivalents thereof can be configured to be used in either an "open" system (e.g., see FIGS. 3B-3C, 4B-4C and 5A-5C) or a "closed" system (e.g., see FIGS. 2C-2D, 6B and 7B) to separate cells from microcarriers or spheroids in a liquid. It should also be appreciated that any of the aforementioned cell separation devices 100, 200, 300, 400, 500, 600 and 700 or equivalents thereof can be used to separate cells from a liquid as discussed below with respect to FIG. 8.

Figure 8:
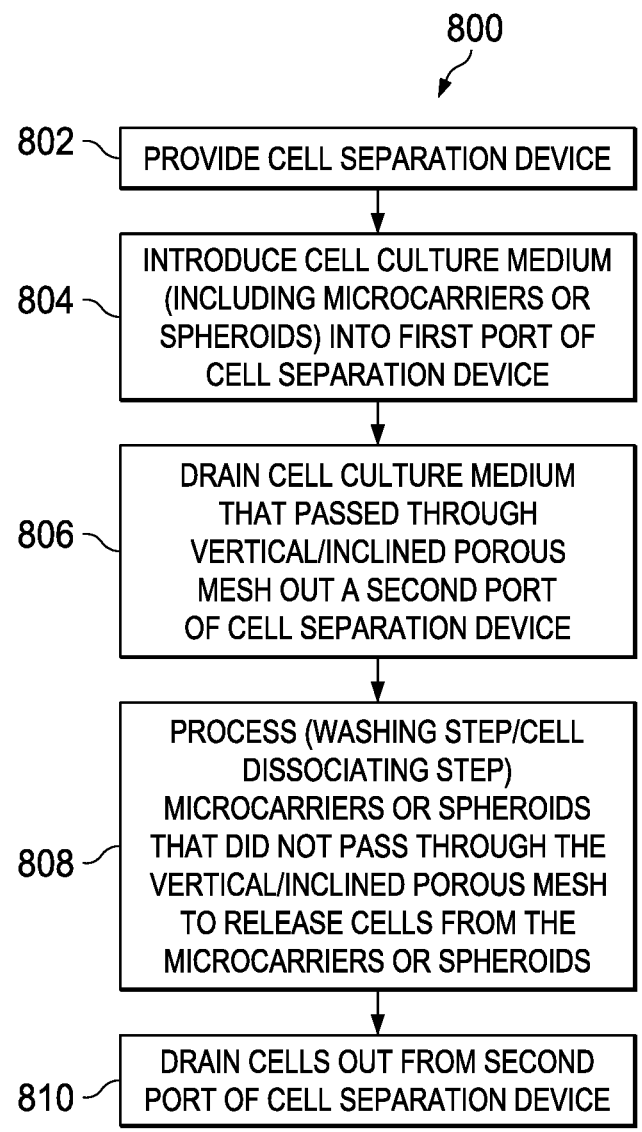

Referring to FIG. 8, there is a method 800 for using the cell separation device 100, 200, 300, 400, 500, 600 and 700 to separate cells from microcarriers or spheroids in a liquid (e.g., cell culture medium, buffered saline). At step 802, provide the cell separation device 100, 200, 300, 400, 500, 600 and 700. At step 804, introduce the liquid (including microcarriers or spheroids) through the first port 106, 206, 306, 406, 506, 606 and 706 into the first compartment 112, 212, 312, 412, 512, 612 and 712 of the cavity 110, 210, 310, 410, 510, 610 and 710 of the cell separation device 100, 200, 300, 400, 500, 600 and 700. At step 806, drain the liquid that passed through the inclined or vertical porous mesh 102, 202, 302, 402, 502, 602 and 702 out of the second port 108, 208, 308, 408, 508, 608 and 708 of the cell separation device 100, 200, 300, 400, 500, 600 and 700. After step 806, the microcarriers or spheroids will remain in the cell separation device 100, 200, 300, 400, 500, 600 and 700 due to the vertical or inclined porous mesh 102, 202, 302, 402, 502, 602 and 702. At step 808, process (e.g., washing step and cell dissociating step) the microcarriers or spheroids that did not pass through the vertical or inclined porous mesh 102, 202, 302, 402, 502, 602 and 702 out the second port 108, 208, 308, 408, 508, 608 and 708 to release the cells from the microcarriers or spheroids. At step 810, drain the cells out of the second port 108, 208, 308, 408, 508, 608 and 708 of the cell separation device 100, 200, 300, 400, 500, 600 and 700. The cell separation device 100, 200, 300, 400, 500, 600 and 700 by having the vertical or inclined porous mesh 102, 202, 302, 402, 502, 602 and 702 is a marked-improvement over the traditional cell separation devices in that when the new cell separation device 100, 200, 300, 400, 500, 600 and 700 is used the flow of the liquid through the vertical or inclined porous mesh 102, 202, 302, 402, 502, 602 and 702 is no longer easily blocked as in the traditional cell separation device because the microcarriers or spheroids will no longer block a majority of the pores within the vertical or inclined porous mesh 102, 202, 302, 402, 502, 602 and 702 due to gravity as they would in the horizontal porous mesh of the traditional cell separation devices.

The following is a discussion about harvest experiments that were performed using prototype "open-system" cell separation devices 300, 400 and 500 (see FIGS. 3A, 4A and 5A) and a prototype "closed-system" cell separation device 600 (see FIGS. 6A-6B). In the following discussion, the term microcarriers has been abbreviated as MCs, milliliter has been abbreviated mL and centrifuge tube has been abbreviated CT. All experiments were carried out in a biological hood. The cells were seeded at an initial density of 50,000 cells per square centimeter of total microcarrier surface area. The microcarriers were cultured in Corning® Spinner Flasks. One spinner flask was used for assessing the harvest for the control method (no cell separation device) and all of the prototype "open-system" cell separation devices 300, 400 and 500. The microcarriers in medium were mixed well and then measured into individual centrifuge tubes to be used for each cell separation device 300, 400 and 500. A separate spinner flask culture was used to create the harvest for the prototype "closed-system" cell separation device 600. The methods for harvesting are described below for the control and for each of the tested prototype cell separation devices 300, 400, 500 and 600.

Control: The control harvest utilized a standard method without a separation device. Step 1) 50 mL of MCs in medium were added to a CT and let to stand for 5 minutes to settle the MCs. Step 2) The medium was aspirated off the MCs. 10 mL of PBS (washing solution) was added to the CT and the MCs re-suspended, then allowed to settle. Step 3) The PBS was aspirated off of the settled MCs, and then another PBS wash was performed as stated in Step 2. Step 4) The PBS was aspirated off the settled MCs and 5 mL of trypsin (cell dissociation reagent) was added, the MCs were re-suspended and then allowed to incubate for 5 minutes. The trypsin/cell solution was aspirated off the settled MCs and placed in a sterile CT. Step 5) 2 more PBS washes were performed using 5 mL each time as stated in step 2, but the aspirated PBS and cells were added to the CT containing the previously aspirated cells and trypsin. Step 6) A final wash of the MCs was conducted using medium with fetal bovine serum (FBS) to inactivate the trypsin. This was added to the cell solution test tube to bring the total volume to 20 mL. The total time to perform cell separation from MCs was about 40 minutes. Instead of allowing the cells to settle, the CT could have been centrifuged following each manipulation, but that would not have decreased the total amount of time to perform the separation.

Prototype Cell Separation Device 300: Step 1) The caps 324 and 326 were removed from the cell separation device 300 and the second port 308 (in position 1—FIG. 3B) was placed into an empty centrifuge tube (waste CT). A stripette was used to aspirate 25 mL of MCs and medium from the MC-containing centrifuge tube. This volume was dispensed through the first port 306 into the corner of the cell separation device 300 where the inclined porous mesh 302 meets the sidewall. The medium flowed through the cell separation device 300 into the waste CT in which it was positioned, leaving the MCs in the corner of the cell separation device 300 next to the porous mesh 302 where they were placed. Step 2) The cell separation device 300 was lifted out of the waste CT and placed on the bench-top so the cell separation device 300 containing the MCs rested on its side (position 2—FIG. 3C). 10 mL of phosphate buffered saline (PBS) was added through the first port 306, and the MCs re-suspended in the PBS to be washed. The cell separation device 300 was held upright (position 1) over the waste CT and the PBS flowed through the porous mesh 302 into the waste CT, leaving the MCs behind. The wash was repeated (repeat step 2). Step 3) The cell separation device 300 was again placed with its side on the bench-top (position 2). 5 mL of trypsin was added and the MCs re-suspended. The cell separation device 300 with the MCs was left to incubate in the trypsin for 5 minutes with periodic agitation to re-suspend the MCs. After the 5 minute incubation, the trypsin and cells were allowed to flow through the porous mesh 302 by placing the second port 308 into a fresh CT and standing the cell separation device 300 upright (position 1). Step 4) After evacuating the fluid and cells from the cell separation device 300 into the CT, the cell separation device 300 was lifted out and placed on the side with the MCs (position 2). 5 mL of PBS was added, and the MCs washed. The PBS was added to the cell-containing CT. The wash was repeated using 5 mL of PBS and then 5 mL of medium containing fetal bovine serum (FBS) to inactivate the trypsin. These volumes were both added to the cell-containing CT (Total cell volume=20 mL). Alternatively, a reagent (such as TrypLE™) could be used to remove the cells from the MCs instead of trypsin that does not need to be inactivated, eliminating the requirement for FBS containing medium. The total time to perform the separation was about 12 minutes.

Prototype Cell Separation Device 400: Step 1) The caps 424 and 426 were removed from the cell separation device 400. The cell separation device 400 was placed on the bench-top on its side (position 2—FIG. 4C). Using a stripette, 25 mL of MCs in medium were placed through the first port 406 into the cell separation device 400, while tipping the cell separation device 400 to position 1 (FIG. 4B) so that the fluid was free to move through the porous mesh 402 that is located between the two compartments 412 and 414. The medium was aspirated through the second port 408 to a waste container. Step 2) With the cell separation device 400 in position 1, 10 mL of PBS was added through the first port 406 and the cell separation device 400 was tipped side-to-side to move the fluid to wash the MCs, then tipped to position 2 to evacuate the fluid through the porous mesh 402 into the next compartment 414. The fluid was aspirated out through the second port 408 into a waste container. This wash was repeated. Step 3) With the cell separation device 400 in position 1, 5 mL of trypsin was added through the first port 406 and the MCs re-suspended. The MCs were left to incubate in the trypsin for 5 minutes with periodic agitation to re-suspend the MCs. After the 5 minute incubation, the cell separation device 400 was tipped and the trypsin and cells were allowed to flow through the porous mesh 402 into the next compartment 414 where they were collected by aspiration through the second port 408. The cells and fluid were placed in a sterile CT. Step 4) 5 mL of PBS was added to the cell separation device 400 in position 1, and the MCs washed by tipping the device side-to-side. The cell separation device 400 was tipped to position 2 and the PBS and cells were allowed to flow through the porous mesh into the next compartment 414 where they were collected by aspiration through the second port 408. The PBS and cells were added to the cell-containing CT. The wash was repeated as stated using 5 mL of PBS and then 5 mL of medium containing fetal bovine serum to inactivate the trypsin. These volumes were both added to the cell-containing CT (Total cell volume=20 mL). The total time to perform the separation was about 12 minutes.

Prototype Cell Separation Device 500: Step 1) The caps 524 and 526 were removed from the cell separation device 500 in position 2 (FIG. 5C) and using a stripette, 25 mL of MCs in medium were placed through the first port 506 into the cell separation device 500. The cell separation device 500 was tipped to position 3 (FIG. 5D) so the fluid moved through the porous mesh 502 and into the second compartment 514 where it could be aspirated to waste through the second port 508. Step 2) An additional 25 mL of MCs in medium was added through the first port 506 with the cell separation device 500 in position 2, then tipped to position 3 so that the fluid could be aspirated to waste through the second port 508. Step 3) With the cell separation device 500 in position 2, 10 mL of PBS was added through the first port 506 and the cell separation device 500 was tipped side-to-side to move the fluid to wash the MCs, then tipped to position 3 to evacuate the fluid through the porous mesh 502 into the next compartment 514. The fluid was aspirated out through the second port 508 into a waste container. This wash was repeated. Step 4) With the cell separation device 500 in position 2, 5 ml of trypsin was added to re-suspend the MCs, then incubated for 5 minutes in position 1, with occasional agitation to re-suspend the MCs. After incubation, the cell separation device 500 was tipped to position 3 and the cells and fluid aspirated from the second port 508 and placed in a sterile CT. Step 5). 3 MC washes were conducted as discussed in Step 3; twice using 5 mL of PBS, then once with 5 mL in media containing FBS. All washes and cells were collected into the same CT (Total cell volume=20 mL). The total time to perform the separation was about 15 minutes.

Prototype Cell Separation Device 400 (this experiment was different than the previous experiment which also used prototype cell separation device 400): Step 1) The caps 424 and 426 were removed from the cell separation device 400. The cell separation device 400 was placed on the bench-top on its side (in position 2—FIG. 4C). Using a stripette, 25 mL of MCs in medium were placed through the first port into the upper compartment 412 of the cell separation device 400. This created an airlock so that a vacuum was created when a syringe was applied to the second port 408, so that the fluid was free to move through the porous mesh 402 that is located between the two compartments 412 and 414 and into the lower compartment 414. The medium was aspirated through the second port 408 to a waste container. Step 2) With cell separation device 400 in position 1 (FIG. 4B), 10 mL of PBS was added through the first port 406 and the cell separation device 400 was tipped side-to-side to move the fluid to wash the MCs, then tipped to position 2 to evacuate the fluid through the porous mesh 402 into the next compartment 414. The fluid was aspirated out through the second port 408 into a waste container. This wash was repeated. Step 3) With the cell separation device 400 in position 1, 5 mL of trypsin was added through the first port 406 and the MCs re-suspended. The MCs were left to incubate in the trypsin for 5 minutes with periodic agitation to re-suspend the MCs. After the 5 minute incubation, the cell separation device 400 was tipped and the trypsin and cells were allowed to flow through the porous mesh 402 into the next compartment 414 where they were collected by aspiration through the second port 408. The cells and fluid were placed in a sterile CT. Step 4) 5 mL of PBS was added to cell separation device 400 in position 1, and the MCs washed by tipping the cell separation device 400 side-to-side. The cell separation device 400 was tipped to position 2 and the PBS and cells were allowed to flow through the porous mesh 402 into the next compartment 414 where they were collected by aspiration through the second port 408. The PBS and cells were added to the cell-containing CT. The wash was repeated as stated using 5 mL of PBS and then 5 mL of medium containing fetal bovine serum to inactivate the trypsin. These volumes were both added to the cell-containing CT (Total cell volume=20 mL). The total time to perform the separation was about 13 minutes due to the airlock that formed.

Prototype Closed-system Cell Separation Device 600: Step 1) With the cell separation device 600 in position 1 (upright as shown in FIG. 6B), clamps were opened to permit fluid flow from the spinner flask 678 to the cell separation device 600 to the waste container 674. Other clamps remained closed. The MCs and medium were forced up the dip tube and flowed through the system to the porous mesh 602 of the cell separation device 600 by pressurization. The porous mesh 602 stopped the MCs, while the medium flowed through to the waste container 674. Step 2) Vents were unclamped, as well as the fluid pathway from the PBS container 672 to the spinner flask 678. Other clamps were closed. PBS flowed into the spinner flask 678 by gravity through a dip tube. The spinner flask 678 was swirled to re-suspend the remaining MCs. Clamps were closed on the vents and opened for the pathway from the spinner flask 678 to the cell separation device 600 (now in side-ways position). Pressurization was again initiated to force the PBS/MCs out of the spinner flask 678 to the cell separation device 600. Pressure was turned-off as the PBS and MCs made their way into the cell separation device 600. Vent clamps were opened. The cell separation device 600 was tilted side-to-side to wash the MCs in the collected PBS. Step 2 was repeated to capture and rinse all the MCs. The cell separation device 600 was moved to position 1 (upright as shown in FIG. 6B) and the clamp from the cell separation device 600 to the waste container 674 was opened. PBS in the cell separation device 600 was sent to waste container 674. Step 3). The cell separation device 600 was placed in position 2 (sideways). Vents were unclamped, as well as the fluid pathway from the TrypLE container 670 to the cell separation device 600. Other clamps were closed. TrypLE flowed into the cell separation device 600 by gravity. The cell separation device 600 was tipped side-to-side to re-suspend the MCs in the TrypLE, then left to incubate for 5 minutes with occasional agitation. The fluid pathway from the cell separation device 600 to the cell collection container 676 was opened, the cell separation device 600 was placed in position 1 (upright as shown in FIG. 6B), and the cells and TrypLE were allowed to flow into the cell collection container 676. Step 4) The cell separation device 600 was placed in position 2 (sideways). Vents remained unclamped, as well as the fluid pathway from the PBS container 672 to the cell separation device 600. Other clamps were closed. PBS flowed into the cell separation device 600 by gravity. The MCs were re-suspended in the PBS and washed. The fluid pathway from the cell separation device 600 to the cell collection container 676 was opened, the cell separation device 600 was placed in position 1, and the cells and PBS allowed to flow into the cell collection container 676. This step was repeated to create a total cell volume of 200 mL. The total time to perform the separation was about 20 minutes.

Results of Experiments:

0.2 mL of the cell suspension obtained from the control and each of the prototype separation devices 300, 400, 500 and 600 was loaded into NucleoCounter® cassettes to determine the number of cells collected per mL, the cell viability, and the % of cells remaining in clumps (clusters of cells). The results from the control and each of the prototype separation devices 300, 400, 500 and 600 are provided in TABLE #1 as follows:

TABLE #1

| Cell/Microcarrier (MC) Separations | | | | | | | |
|---|---|---|---|---|---|---|---|
| Cell Separation Device (CSD) | Initial Volume (mL) | Total cm² MC | Cells/mL | Viability (%) | Total Viable Cells | % of Control/Vol | % Clumps |
| Control | 50 | 500 | $2.12 \times 10^6$ | 99.7 | $4.24 \times 10^7$ | 100 | 7 |
| CSD 300 | 25 | 250 | $1.2 \times 10^6$ | 99.7 | $2.4 \times 10^7$ | 113 | 10 |
| CSD 400 | 25 | 250 | $6.57 \times 10^5$ | 99.6 | $1.31 \times 10^7$ | 62 | 16 |
| CSD 500 | 50 | 500 | $1.8 \times 10^6$ | 98.9 | $3.6 \times 10^7$ | 86 | 19 |
| CSD 400 | 25 | 250 | $8.8 \times 10^5$ | 99.5 | $1.59 \times 10^7$ | 75 | 20 |
| Closed CSD 600 | 200 | 2000 | $6.93 \times 10^5$ | 98.1 | $1.37 \times 10^8$ | 100 | 1 |

Note:
In these experiments, each of the prototype cell separation devices 300, 400, 500 and 600 required small modifications in the procedure used to first separate microcarriers from the medium, and then the cells from the microcarriers. It is also assumed that since spheroids are similar to the size of microcarriers that the results for separating spheroids from medium and then reducing the spheroids to single cells would be accomplished in a similar fashion as the microcarriers.

CONCLUSIONS

All cell viabilities were very good. The open-system cell separation devices 300 and 500 were the easiest to handle and appeared to have the least fluid retention since the greatest number of cells were harvested with these separation devices. The cell separation device 300 actually harvested a greater number of cells than the control. This is possible because there can be a loss of MCs during each aspiration step following the control protocol. The amount of time required to harvest the cells was the biggest difference between the control and the tested separation devices 300, 400, 500 and 600. There was an occasional air-lock that prevented fluid flowing automatically through the system associated with the closed-system cell separation device 600, but this was overcome by closing vents and momentarily turning on pressurization. The system associated with the closed-system cell separation device 600 can also be configured to use a vacuum to draw fluid through the system instead of pressurization (see FIG. 7B). There are potentially other designs that could be useful for the separation devices, such as side-by side compartments with the mesh in-between.

In view of the foregoing, there is disclosed a cell separation device that uses a vertical or inclined porous mesh to capture microcarriers or spheroids within a vessel, where they can then be easily washed and treated to either remove the cells from the microcarriers or convert the spheroids into a single cell suspension. The device can be made as an open or closed system. The device may be filled by pouring, gravity, perfusion, vacuum or by pressurization of the source vessel. The device can be structured so that it is easily integrated into a perfusion bioreactor system. The incline or vertical positioning of the porous mesh within the device prevents the microcarriers or spheroids from blocking the pores of the mesh to enhance fluid flow and cell separation. The design of the device enables the liquid (e.g., cell culture medium, buffered saline) to flow over the inclined or vertical mesh such that the microcarriers or spheroids roll off of the mesh and can still be retained in the device. The device is self-contained and after isolating the microcarriers or spheroids on one side of the porous mesh, inverting the device permits further manipulation. The cells may be washed and released from the microcarriers in the device, and then collected by perfusing them out of the device. A single cell suspension can be created from the spheroids in the device and then the cells can be retained or released from the device. The device is self-contained and can potentially be used to transport cells for therapy to the site of administration. The device can be many shapes and scaled in size as needed. The device may be a rigid vessel or a flexible vessel. The device may have an outer housing for stabilization or it can be made without an outer housing as desired. The device can be manufactured using all the conventional methods for forming and assembling devices from plastic materials or other types of materials. To enhance desired attributes the device may be coated or treated. The porous mesh or membrane can be made from polymer, metal or glass or composites thereof and the pore sizes can range, for example, from about 12 to 200 microns.

According to an aspect (1) of the present disclosure, a cell separation device configured for separating cells from microcarriers or spheroids in a liquid. The cell separation device comprises: a vessel comprising a first port, a second port, and a cavity; and a porous mesh disposed within the cavity to divide the cavity into a first compartment and a second compartment, wherein the first port is in communication with the first compartment of the cavity, the first port located to a first side of the porous mesh, wherein the second port is in communication with the second compartment of the cavity, the second port located to a second side of the porous mesh, and wherein the porous mesh is positioned within the cavity to have a substantially vertical orientation or an inclined orientation with respect to a flow of liquid through the porous mesh.

According to another aspect (2) of the present disclosure, the cell separation device of aspect (1) is provided, wherein the first port is located at one end of the vessel and the second port is located at an opposing end of the vessel.

According to another aspect (3) of the present disclosure, the cell separation device of aspect (2) is provided, wherein the first port and the second port are off-set from one another on the vessel such that the porous mesh has the substantially vertical orientation within the cavity when (1) the first port is located in a substantially upward orientation and the second port is located in a substantially downward orientation, or (2) the first port is located in the substantially downward orientation and the second port is located in the substantially upward orientation.

According to another aspect (4) of the present disclosure, the cell separation device of aspect (2) is provided, wherein the first port and the second port are in-line with one another on the vessel such that the porous mesh has the inclined orientation within the cavity when (1) the first port is located in a substantially upward orientation and the second port is located in a substantially downward orientation, or (2) the first port is located in the substantially downward orientation and the second port is located in the substantially upward orientation.

According to another aspect (5) of the present disclosure, the cell separation device of aspect (1) is provided, wherein the first port and the second port are both positioned on one side of the vessel and the porous mesh has the substantially vertical orientation within the cavity when (1) the first port and the second port are located in a substantially upward orientation, or (2) the first port and the second port are located in a substantially downward orientation.

According to another aspect (6) of the present disclosure, the cell separation device of any of aspects (1)-(5) is provided, further comprising: a first cap attachable to the first port; and a second cap attachable to the second port.

According to another aspect (7) of the present disclosure, the cell separation device of any of aspects (1)-(6) is provided, further comprising: a first flow control system attached to the first port and external equipment; and a second flow control system attached to the second port and external equipment.

According to another aspect (8) of the present disclosure, the cell separation device of any of aspects (1)-(7) is provided, wherein the porous mesh comprises pores therein with sizes ranging from about 12 microns to about 200 microns.

According to another aspect (9) of the present disclosure, the cell separation device of any of aspects (1)-(8) is provided, further comprising: an outer housing surrounding at least a portion of the vessel.

According to another aspect (10) of the present disclosure, the cell separation device of any of aspects (1)-(9) is provided, further comprising: a ring stand coupled to the vessel, the ring stand configured to facilitate movement and rotation of the vessel.

According to another aspect (11) of the present disclosure, a method for separating cells from microcarriers or spheroids in a liquid is provided. The method comprises: introducing liquid through a first port of a vessel of a cell separation device, the vessel further comprising a second port, and a cavity, wherein a porous mesh is disposed within the cavity to have a substantially vertical or an inclined orientation with respect to a flow of the liquid through the porous mesh and to divide the cavity into a first compartment and a second compartment, wherein the first port located to a first side of the porous mesh, and wherein the first port is in communication with the first compartment of the cavity and the second port is in communication with the second compartment of the cavity; draining the liquid that passes through the porous mesh out of the second port; processing the microcarriers or spheroids that does not pass through the porous mesh to release the cells from the microcarriers or spheroids; and draining the cells out of the second port.

According to another aspect (12) of the present disclosure, the method of aspect (11) is provided, wherein processing the microcarriers or spheroids further comprises washing the microcarriers or spheroids and then dissociating cells from the microcarriers or spheroids.

According to another aspect (13) of the present disclosure, the method of aspect (12) is provided, wherein washing the microcarriers or spheroids comprises: adding a washing solution to the cavity; moving the vessel; and draining the washing solution out of the second port.

According to another aspect (14) of the present disclosure, the method of aspect (12) is provided, wherein dissociating cells from the microcarriers or spheroids comprises: adding a cell dissociation reagent to the cavity; and moving the vessel, and wherein draining the cells out of the second port further comprises draining the cell dissociation reagent out of the second port.

According to another aspect (15) of the present disclosure, the method of any of aspects (11)-(14) is provided, wherein the separation device is an open-system cell separation device that is not directly connected to external devices.

According to another aspect (16) of the present disclosure, the method of any of aspects (11)-(14) is provided, wherein the separation device is a closed-system cell separation device that is directly connected to external devices.

According to another aspect (17) of the present disclosure, the method of any of aspects (11)-(16) is provided, wherein the first port is located at one end of the vessel and the second port is located at an opposing end of the vessel.

According to another aspect (18) of the present disclosure, the method of aspect (17) is provided, wherein the first port and the second port are off-set from one another on the vessel such that the porous mesh has the substantially vertical orientation within the cavity when (1) the first port is located in a substantially upward orientation and the second port is located in a substantially downward orientation, or (2) the first port is located in the substantially downward orientation and the second port is located in the substantially upward orientation.

According to another aspect (19) of the present disclosure, the method of aspect (17) is provided, wherein the first port and the second port are in-line with one another on the vessel such that the porous mesh has the inclined orientation within the cavity when (1) the first port is located in a substantially upward orientation and the second port is located in a substantially downward orientation, or (2) the first port is located in the substantially downward orientation and the second port is located in the substantially upward orientation.

According to another aspect (20) of the present disclosure, the method of any of aspects (11)-(16) is provided, wherein the first port and the second port are both positioned on one side of the vessel and the porous mesh has the substantially vertical orientation within the cavity when (1) the first port and the second port are located in a substantially upward orientation, or (2) the first port and the second port are located in a substantially downward orientation.

It will be appreciated that the various disclosed embodiments may involve particular features, elements or steps that are described in connection with that particular embodiment. It will also be appreciated that a particular feature, element or step, although described in relation to one particular embodiment, may be interchanged or combined with alternate embodiments in various non-illustrated combinations or permutations.

It is also to be understood that, as used herein the terms "the," "a," or "an," mean "at least one," and should not be limited to "only one" unless explicitly indicated to the contrary. Thus, for example, reference to "an opening" includes examples having two or more such "openings" unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All numerical values expressed herein are to be interpreted as including "about," whether or not so stated, unless expressly indicated otherwise. It is further understood, however, that each numerical value recited is precisely contemplated as well, regardless of whether it is expressed as "about" that value. Thus, "a dimension less than 10 mm" and "a dimension less than about 10 mm" both include embodiments of "a dimension less than about 10 mm" as well as "a dimension less than 10 mm."

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method comprising A+B+C include embodiments where a method consists of A+B+C, and embodiments where a method consists essentially of A+B+C.

Although multiple embodiments of the present disclosure have been illustrated in the accompanying Drawings and described in the foregoing Detailed Description, it should be understood that the disclosure is not limited to the disclosed embodiments, but is capable of numerous rearrangements, modifications and substitutions without departing from the disclosure as set forth and defined by the following claims.

The invention claimed is:

1. A method for separating cells from microcarriers or spheroids in a liquid media, the method comprising:
  preparing a vessel of a cell separation device to receive a liquid media, wherein the vessel comprises a first port and a second port, and a cavity with a porous mesh disposed therein,
    wherein the porous mesh is positioned within the cavity to divide the cavity into a first compartment and a second compartment, wherein the first port is in direct communication with the first compartment and the second port is in direct communication with the second compartment and wherein the porous mesh is also positioned to not be horizontally aligned to the second port opening,
    wherein the cell separation device is rotatable so that a top surface of the vessel can become a bottom surface and
    wherein the liquid media is comprised of cells adhered to microcarriers or spheroids
  orienting the vessel in a first position such that liquid in the cavity will drain from the second port;
  introducing the liquid media into the first port;

collecting microcarriers or spheroids from the liquid media in the first compartment that cannot filter through the porous mesh and draining any portion of the liquid media that passes through the porous mesh out of the second port;

repositioning the vessel to a second position wherein any liquid added into the cavity through the first port will cover collected microcarriers or spheroids in the first compartment before reaching the second port;

adding a volume of a dissociation reagent sufficient to cover collected microcarriers or spheroids in the first compartment to release the cells from the microcarriers or spheroids; and repositioning the vessel back to the first position and collecting the cells out of the second port.

2. The method of claim 1, wherein the microcarriers or spheroids are washed prior to adding the volume of dissociation reagent.

3. The method of claim 2, wherein washing the microcarriers or spheroids comprises:

orienting the vessel to the second position;

adding a washing solution to the cavity;

moving the vessel back to the first position; and draining the washing solution out of the second port.

4. The method of claim 1, wherein the separation device is an open-system cell separation device that is not directly connected to external devices.

5. The method of claim 1, wherein the separation device is a closed-system cell separation device that is directly connected to external devices.

6. The method of claim 1, wherein the first port is located at one end of the vessel and the second port is located at an opposing end of the vessel.

7. The method of claim 6, wherein the first port and the second port are off-set from one another on opposing ends of the vessel such that the porous mesh is substantially perpendicular within the cavity with respect to the second port opening.

8. The method of claim 6, wherein the first port and the second port are in-line with one another on opposing ends of the vessel such that the porous mesh has an inclined orientation with respect to the second port opening.

9. The method of claim 1, wherein the first port and the second port are both positioned on one side of the vessel and the porous mesh is substantially vertical within the cavity when (1) the first port and the second port are located in a substantially upward orientation, or (2) the first port and the second port are located in a substantially downward orientation.

* * * * *